(12) United States Patent
Ernst et al.

(10) Patent No.: US 7,566,459 B2
(45) Date of Patent: Jul. 28, 2009

(54) MODIFIED MYCOBACTERIUM TUBERCULOSIS STRAINS AND USES THEREOF

(75) Inventors: Joel D. Ernst, New York, NY (US); Niaz Banaiee, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/362,539

(22) Filed: Feb. 27, 2006

(65) Prior Publication Data

US 2007/0026020 A1 Feb. 1, 2007

Related U.S. Application Data

(60) Provisional application No. 60/657,152, filed on Feb. 28, 2005.

(51) Int. Cl.
*A61K 39/04* (2006.01)
*A61K 49/00* (2006.01)
*C07H 21/04* (2006.01)
*C07H 21/02* (2006.01)

(52) U.S. Cl. .................. 424/248.1; 536/23.1; 536/23.7; 424/9.1; 424/9.2; 424/93.1; 424/93.2; 424/234.1; 424/278.1

(58) Field of Classification Search .................. 424/9.1, 424/9.2, 93.1, 93.2, 234.1, 248.1, 278.1; 536/23.1, 23.7
See application file for complete search history.

(56) References Cited

OTHER PUBLICATIONS

Wiegeshaus et al., "Evaluation of the Protective Potency of New Tuberculosis Vaccines", Review of Infectious Diseases, vol. 11, Supplement 2, pp. S484-S490, Mar.-Apr. 1989.*

Sander, P., et al. Lipoprotein processing is required for virulence of Mycobacterium tuberculosis. Molecular Microbiology, vol. 52, No. 6, pp. 1543-1552, Jun. 2004.*

Nagabhushanam, V., et al. Innate inhibition of adaptive immunity: Mycobacterium tuberculosis-induced IL-6 inhibits macrophage responses to IFN-gamma. The Journal of Immunology, vol. 171, pp. 4750-4757, 2003.*

Ting, "Mycobacterium tuberculosis Inhibits IFN-gamma Transcriptional Responses Without Inhibiting Activation of STAT1," J. Immunol. 163:3898-906 (1999).

Fortune, "Mycobacterium tuberculosis Inhibits Macrophage Responses to IFN-gamma Through Myeloid Differentiation Factor 88-dependent and -independent Mechanisms," J. Immunol. 172:6272-80 (2004).

* cited by examiner

*Primary Examiner*—Rodney P. Swartz
(74) *Attorney, Agent, or Firm*—Nixon Peabody LLP

(57) ABSTRACT

The present invention features modified *Mycobacterium tuberculosis* strains which lack a functional lspA gene, and vaccine formulations comprising the same. In many embodiments, a modified *Mycobacterium tuberculosis* strain of the invention comprises deletion or inactivation of the lspA gene and/or one or more non-lspA genes that are involved in *Mycobacterium tuberculosis* inhibition of macrophage responses to IFNγ. The present invention also features methods of using the modified *Mycobacterium tuberculosis* strains to treat or present *Mycobacterium tuberculosis* infection in mammals. In addition, the present invention features methods of using ΔlspA strains to identify non-lspA genes or other cellular components that are involved in *Mycobacterium tuberculosis* proinflammatory stimulation of macrophages or inhibition of macrophage responses to IFNγ.

17 Claims, 11 Drawing Sheets

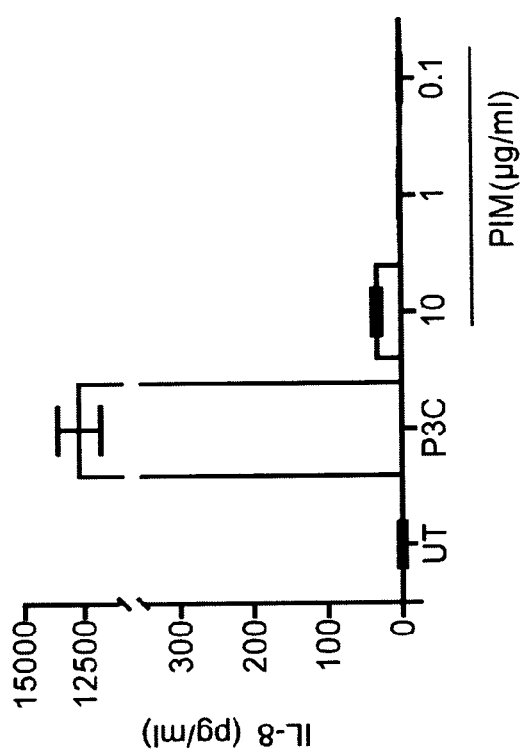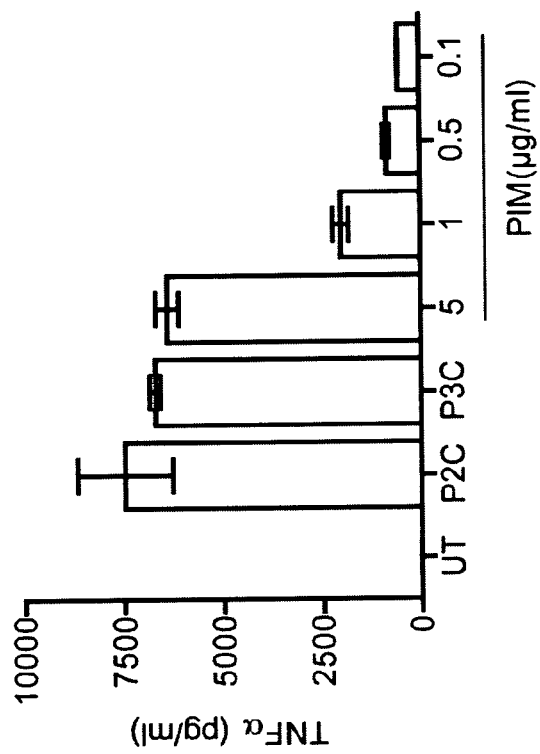

MODIFIED MYCOBACTERIUM TUBERCULOSIS STRAINS AND USES THEREOF

This application claims the benefit of U.S. Provisional Application No. 60/657,152, filed Feb. 28, 2005, the entire content of which is incorporated herein by reference.

This invention was made at least in part by using funds from National Institutes of Health Grants R01 AI46097 and K08 AI061105. Consequently, the federal government has certain rights in this invention.

FIELD OF THE INVENTION

The present invention relates to modified *Mycobacterium tuberculosis* strains which lack a functional lipoprotein signal peptidase, and methods of using these strains to identify *Mycobacterium tuberculosis* genes or other constituents that are involved in *Mycobacterium tuberculosis* inhibition of macrophage responses to IFNγ.

BACKGROUND OF THE INVENTION

*Mycobacterium tuberculosis* is a highly successful pathogen that can infect, persist, and cause progressive disease in humans and experimental animals with apparently normal immune responses. This implies that *Mycobacterium tuberculosis* has evolved mechanisms to avoid elimination by normal mechanisms of immunity. Individuals that are infected with *Mycobacterium tuberculosis* develop apparently appropriate cellular immune responses with priming, expansion, differentiation, and trafficking of antigen specific CD4+ and CD8+ T-cells resulting in interferon gamma (IFNγ) and tumor necrosis factor (TNFα) production at the site of infection. The inability to clear *Mycobacterium tuberculosis* despite this immune response suggests that *Mycobacterium tuberculosis* may interfere with distal effector events. Defective recognition of infected macrophages by T cells and/or defective responses of infected macrophages to effectors of adaptive immunity may contribute to the ability of *Mycobacterium tuberculosis* to persist and progress. One specific mechanism that could permit *Mycobacterium tuberculosis* to avoid elimination by the immune response is inhibition of macrophage responses to IFNγ, an important effector of immunity to intracellular pathogens. Indeed, while IFNγ is capable of stimulating macrophages to kill intracellular Toxoplasma, Leishmania, Legionella, and Chlamydia, it has been reported that IFNγ is incapable of stimulating macrophages to kill *Mycobacterium tuberculosis* in vitro unless IFNγ is used to prime macrophages prior to infection. Moreover, experiments in mice have provided evidence that virulent *Mycobacterium tuberculosis* evades IFNγ-dependent mechanisms of immune control in vivo.

The currently available vaccine against *Mycobacterium tuberculosis* is based on a spontaneously-arising attenuated strain of *Mycobacterium bovis*. However, this vaccine has been insufficient to control the human tuberculosis pandemic, probably as a result of the ability of *Mycobacterium tuberculosis* to evade human immune response. Therefore, there is a need for new vaccines and treatments that can reduce or abrogate *Mycobacterium tuberculosis* evasion of hosts' immune responses.

SUMMARY OF THE INVENTION

The present invention features modified *Mycobacterium tuberculosis* strains which lack a functional lspA gene, and vaccine formulations comprising the same. The present invention also features methods of using ΔlspA strains for the identification of non-lspA genes that are involved in *Mycobacterium tuberculosis* proinflammatory stimulation of macrophages or inhibition of macrophage responses to IFNγ. In addition, the present invention features methods of using ΔlspA strains for the identification of *Mycobacterium tuberculosis* components that contribute to *Mycobacterium tuberculosis* evasion of hosts' immune responses. The present invention further features methods of using ΔlspA strains for the identification of agents that are capable of inhibiting or abrogating the effects of *Mycobacterium tuberculosis* on hosts' immune systems.

In one aspect, the present invention provides modified *Mycobacterium tuberculosis* strains in which the lspA gene is deleted or inactivated. As a non-limiting example, the modified strains are prepared from H37Ra or H37Rv. In many embodiments, the modified strains also include deletion or inactivation of one or more non-lspA genes and have attenuated virulence.

The present invention also provides vaccine formulations comprising the modified *Mycobacterium tuberculosis* strains of the present invention, and methods of using these strains to treat or prevent *Mycobacterium tuberculosis* infection in mammals. The methods typically comprise administering one or more modified *Mycobacterium tuberculosis* strains of the present invention to a mammal under conditions effective to treat or prevent *Mycobacterium tuberculosis* infection. In one embodiment, the mammal being treated is human.

In another aspect, the present invention provides methods for identifying *Mycobacterium tuberculosis* genes whose deletion or inactivation reduces *Mycobacterium tuberculosis* proinflammatory stimulation of macrophages. These methods comprise:

deleting or inactivating one or more non-lspA genes in a background *Mycobacterium tuberculosis* strain that lacks a functional lspA gene; and detecting the TNFα secretion level by macrophages infected with the modified strain (i.e., after the deletion or inactivation of the non-lspA gene(s)).

A reduction in the TNFα secretion level by the macrophages infected with the modified strain, as compared to a control TNFα secretion level (e.g., the TNFα secretion level by macrophages infected with the background strain), is indicative that the non-lspA gene(s) contributes to *Mycobacterium tuberculosis* proinflammatory stimulation of macrophages, and that deletion or inactivation of the non-lspA gene(s) reduces (including abolishes) the proinflammatory stimulation. Preferably, the modified strain can reduce the proinflammatory stimulation by at least 10%, 20%, 30%, 40%, 50%, 60%, 70%, 80%, 90%, or more, as compared to the background strain.

In yet another aspect, the present invention provides methods for identifying *Mycobacterium tuberculosis* genes whose deletion or inactivation reduces *Mycobacterium tuberculosis* inhibition of macrophage responses to IFNγ. These methods comprise:

deleting or inactivating one or more non-lspA genes in a background *Mycobacterium tuberculosis* strain that lacks a functional lspA gene;

contacting macrophages infected with the modified strain with IFNγ; and detecting the IFNγ response level of the macrophages.

A reduction in the IFNγ response level of the macrophage infected with the modified strain, as compared to a control IFNγ response level (e.g., the IFNγ response level of macrophages infected with the background strain), indicates that the non-lspA gene(s) contributes to *Mycobacterium tuberculosis* inhibition of macrophage responses to IFNγ, and that deletion or inactivation of the non-lspA gene(s) reduces (including abolishes) the inhibition. Preferably, the modified strain can reduce the inhibition by at least 10%, 20%, 30%, 40%, 50%, 60%, 70%, 80%, 90%, or more, as compared to the background strain.

Any method known in the art can be used to measure the IFNγ response level of macrophages. In one embodiment, the IFNγ response level is determined by measuring MHC class II surface expression level or CIITA MRNA level in the macrophages.

The present invention also features methods for identifying *Mycobacterium tuberculosis* genes whose deletion or inactivation reduces *Mycobacterium tuberculosis* TLR2 agonist activity. These methods comprise:

deleting or inactivating one or more non-lspA genes in a background *Mycobacterium tuberculosis* strain which lacks a functional lspA gene; and detecting the TLR2 activation level in macrophages infected with the modified strain.

A reduction in the TLR2 activation level in the macrophages infected with the modified strain, as compared to a control TLR2 activation level (e.g., the TLR2 activation level of macrophages infected with the background strain), is indicative that deletion or inactivation of the non-lspA gene(s) can reduce (including abolish) *Mycobacterium tuberculosis* TLR2 agonist activity. Preferably, the modified strain can reduce *Mycobacterium tuberculosis* TLR2 agonist activity by at least 10%, 20%, 30%, 40%, 50%, 60%, 70%, 80%, 90%, or more, as compared to the background strain.

The TNFα secretion level, IFNγ response level, or TLR2 activation level can be determined by averaging the results of individual macrophage cultures. Any averaging method known in the art may be used for this purpose. The TNFα secretion level, IFNγ response level, or TLR2 activation level can also be determined based on the results of single macrophage cultures.

In still another aspect, the present invention features methods for identifying *Mycobacterium tuberculosis* constituents capable of inhibiting macrophage response to IFNγ. These methods comprise:

isolating a constituent of a *Mycobacterium tuberculosis* strain that lacks a functional lspA gene;

contacting the constituent with macrophages; and detecting the IFNγ response level of the macrophages after the contact.

A reduction in the IFNγ response level of the macrophages treated with the constituent, as compared to a control IFNγ response level (e.g., the IFNγ response level of macrophages that are not treated with the constituent, or the IFNγ response level of macrophages treated with a control agent), is indicative that the constituent being investigated is capable of inhibiting macrophage response to IFNγ. As used herein, a constituent can be, without limitation, a protein, a polysaccharide, a lipid, a glycolipid, a lipoprotein, or a fragment or a mixture thereof. A constituent can also be, without limitation, a fragment of the cell wall, cell membrane or another cellular organelle, a fraction of a bacterial extract, or a mixture thereof.

In addition, the present invention features methods for identifying TLR2 agonists. These methods comprise:

isolating a constituent of a *Mycobacterium tuberculosis* strain that lacks a functional lspA gene;

contacting the constituent with macrophages; and detecting the TLR2 activation level in the macrophages after the contact.

An increase in the TLR2 activation level in the macrophages treated with the constituent, as compared to a control TLR2 activation level (e.g., the TLR2 activation level in macrophages that are not treated with the constituent, or the IFNγ response level of macrophages treated with a control agent), is indicative that the isolated constituent is a TLR2 agonist.

Moreover, the present invention features methods for identifying agents capable of reducing *Mycobacterium tuberculosis* inhibition of macrophage response to IFNγ. The methods comprise:

infecting macrophages with a *Mycobacterium tuberculosis* strain that lacks a functional lspA gene;

contacting or treating the infected macrophages with an agent of interest; and detecting the IFNγ response level of the macrophages after the contact or treatment.

An increase in the IFNγ response level after the contact or treatment, as compared to a control IFNγ response level (e.g., the IFNγ response level of macrophages infected with the same *Mycobacterium tuberculosis* strain but not treated with the agent of interest, or the IFNγ response level of macrophages infected with the same *Mycobacterium tuberculosis* strain and treated with a control agent), is indicative that the agent is capable of reducing *Mycobacterium tuberculosis* inhibition of macrophage response to IFNγ.

The present invention also contemplates pharmaceutical compositions comprising an agent thus identified, and methods of using such an agent to treat or prevent *Mycobacterium tuberculosis* infection in mammals. These methods typically include administering to a mammal in need thereof a therapeutically or prophylactically effective amount of an agent identified according to the present invention.

The present invention further features methods for isolating components for adjuvant therapy. The isolation does not require removal of lipoproteins. These methods typically comprise:

disrupting a modified *Mycobacterium tuberculosis* strain which lacks a functional lspA gene;

fractionating components of the modified strain; and isolating one or more cell wall components for adjuvant therapy.

In one embodiment, the isolation comprises extraction, which may or may not include chemical or enzymatic cleavage(s).

Other features, objects, and advantages of the present invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

In FIG. 5A, RAW264.7 cells were infected with wild type H37Rv (filled squares), ΔlspA (open triangles) or ΔlspAattB::lspA complement (filled triangles) at a range of multiplicities of infection, as indicated. Cell supernatants were harvested after 8 h. In FIG. 5B, RAW264.7 cells were treated with 0.3 µg/ml Mycobacterium tuberculosis whole cell lysates from the indicated strains. Protein concentrations refer to soluble protein in whole cell lysates. Cell supernatants were harvested at the indicated times. Secretion of TNFα into the medium was quantitated by ELISA (mean±SD of triplicate assays). Results are representative of 4 (FIG. 5A) and 2 (FIG. 5B) independent experiments.

In FIG. 7A, bone marrow derived macrophages (BMDM) from C57BL/6 (filled circles) or TLR2$^{-/-}$ (open circles) mice were infected with wild-type H37Rv (solid lines) or the ΔlspA mutant strain (dashed lines) at the indicated MOI. Infection was allowed to proceed for 24 h. In FIG. 7B, BMDM from C57BL/6 (filled circles) or TLR2$^{-/-}$ (open circles) mice were treated with whole cell lysates from wild-type H37Rv (solid lines) or the ΔlspA mutant (dashed lines), at the indicated concentrations, for 24 h. In both FIGS. 7A and 7B, total RNA was harvested after 4 h IFNγ treatment. CIITA expression was assayed by quantitative real-time RT-PCR with primers recognizing all forms of murine CIITA. All values were normalized to GAPDH. Results are shown as fold induction compared to uninfected sample without IFNγ. Results are representative of 3 (FIG. 7A) or 2 (FIG. 7B) independent experiments.

FIGS. 8A, 8B, and 8C show that Mycobacterium tuberculosis phosphatidyl inositol mannan$_{1+2}$ (PIM) inhibits macrophage response to IFNγ. In FIG. 8A, 293-TLR2 cells were left untreated (UT) or were treated with 2 nM Pam$_3$CSK$_4$ (P3C) or the indicated doses of PIM for 24 h. Cell culture supernatants were analyzed by ELISA for human IL-8. Background level of IL-8 secreted into media of untreated cells (47.2 pg/ml) was subtracted from all values. Values shown are the mean of triplicate assays. Overexpression of human CD36 in these cells did not significantly increase the induction of IL-8 secretion in response to these concentrations of PIM. In FIG. 8B, RAW264.7 cells were left untreated or were treated with 2 nM Pam$_2$CSK$_4$ ((S)-[2,3-Bis(palmitoyloxy)-(2-RS)-propyl]-(R)-Cys-(S)-Ser-(S)-Lys$_4$×3 CF3COOH), 2 nM Pam$_3$CSK$_4$ ((S)-[2,3-Bis(palmitoyloxy)-(2-RS)-propyl]-N-palmitoyl-(R)-Cys-(S)-Ser-(S)-Lys$_4$-OH, 3HCl) or the indicated doses of PIM for 8 h. Cell culture supernatants were analyzed by ELISA for murine TNFα. Solvent control (DMSO) did not induce IL-8 or TNFα above background levels. In FIG. 8C, RAW264.7 cells were treated with the indicated doses of PIM for 24 h, followed by 18-24 h treatment with IFNγ. Cells were stained with PE conjugated anti-mouse I-A/I-E, and analyzed by flow cytometry (10,000 total events were counted). Values shown are mean fluorescent intensity (mean±SD of triplicate assays). Solvent control (DMSO) did not inhibit IFNγ-induced MHC Class II expression. Values shown are mean±SD of triplicate assays. Results are representative of 3 (FIG. 8A), 4 (FIG. 8B), and 3 (FIG. 8C) independent experiments.

In FIG. 9A, RAW264.7 cells were treated with γ-irradiated *Mycobacterium tuberculosis* for the indicated times or left untreated ("0"). After *Mycobacterium tuberculosis* treatment, cells were treated with IFNγ for 8 h. Inhibition of CIITA expression was not significantly different at 8 and 24 h. In FIG. 9B, C57BL/6 BMDM cells were pretreated with solvent control (0.02% ethanol) or 500 nM cycloheximide (CHX) for 1 hour before 8 hours of treatment with 3 µg/ml *Mycobacterium tuberculosis* whole cell lysate from wild-type (filled bars), ΔlspA (striped bars), or mock treatment (open bars) in the presence of cycloheximide or ethanol. Cells were then treated with IFNγ for 4 hours. In both FIGS. 9A and 9B, total RNA was harvested after IFNγ treatment. CIITA expression was assayed by quantitative real-time RT-PCR with primers recognizing all forms of murine CIITA. All values were normalized to GAPDH. Results are shown as fold induction compared to uninfected sample without IFNγ. The concentration of CHX used inhibited TNFα production (as a measure of protein synthesis) by *Mycobacterium tuberculosis* treated BMDM by approximately 90%, respectively, while minimizing cell death. Results are representative of 3 (FIG. 9A) or 2 (FIG. 9B) independent experiments.

DETAILED DESCRIPTION

Figure 1:
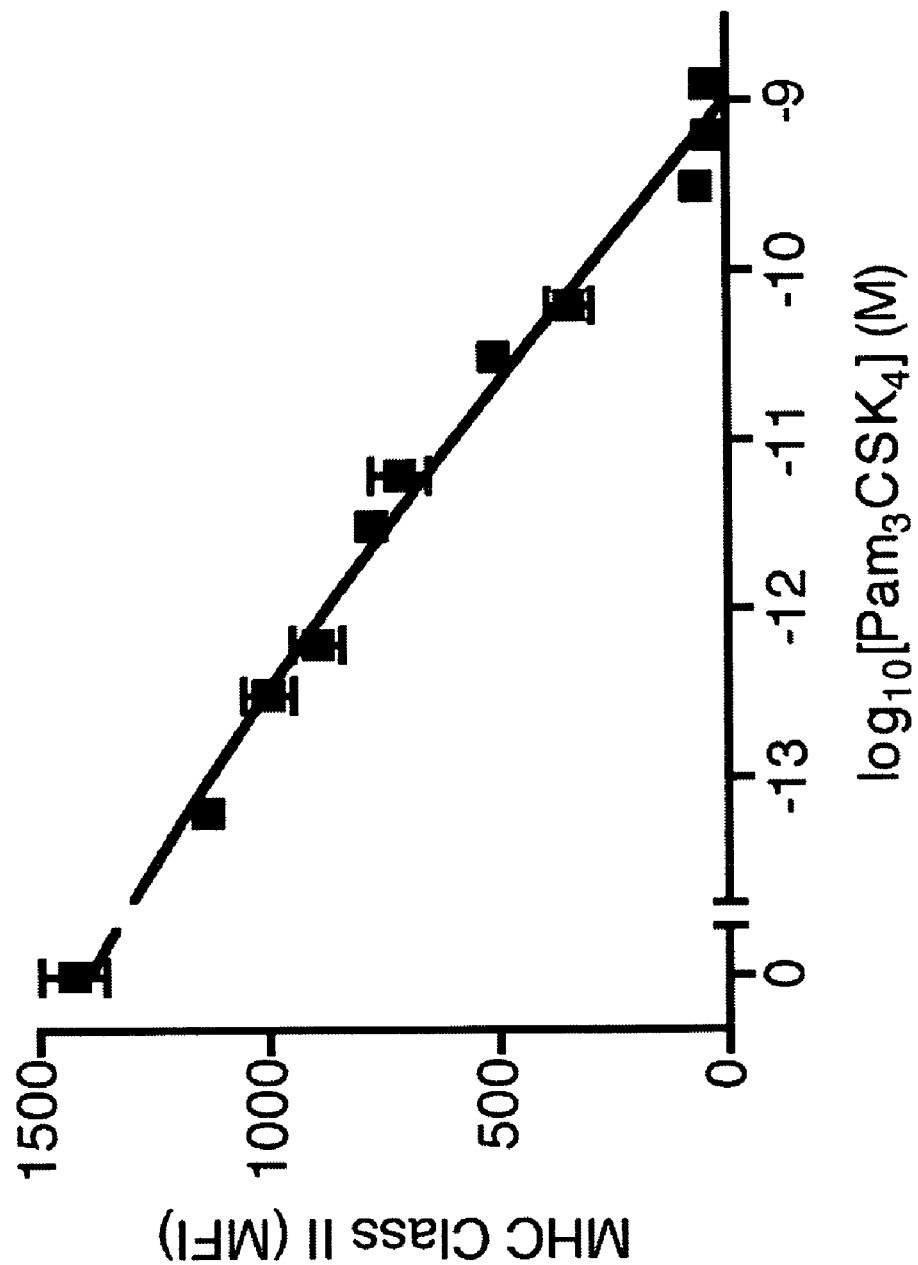
FIG. 1 demonstrates that synthetic triacylated hexapeptide (Pam$_3$CSK$_4$) inhibited macrophage response to IFNγ. RAW264.7 cells were pretreated with media alone ("0") or Pam$_3$CSK$_4$ at the concentrations indicated. 24 h later, cells were treated with IFNγ for 24 hours. Cells were stained with PE conjugated anti-mouse I-A/I-E, and analyzed by flow cytometry (10,000 total events were counted). Values shown are mean fluorescent intensity (mean±SD of triplicate assays). Concordant results were obtained in two other experiments.

The present invention is based on the discovery that *Mycobacterium tuberculosis* employs lipoprotein-dependent and -independent mechanisms to evade immune responses. The present invention features modified *Mycobacterium tuberculosis* strains which are less effective in avoiding elimination by the host's immune system. Preferably, the modified strains of the present invention have attenuated virulence and, therefore, can be used as vaccines against *Mycobacterium tuberculosis* infection. In one embodiment, a modified *Mycobacterium tuberculosis* strain of the present invention lacks a functional lspA gene. This can be achieved through deletion or inactivation of the gene. In another embodiment, a modified *Mycobacterium tuberculosis* strain of the present invention comprises deletion or inactivation of the lspA gene and one or more non-lspA genes that are involved in *Mycobacterium tuberculosis* inhibition of macrophage response to IFNγ. The present invention also features methods for identifying *Mycobacterium tuberculosis* constituents or components that are involved in the proinflammatory stimulation of macrophages or the inhibition of macrophage response to IFNγ.

*Mycobacterium tuberculosis* inhibits human and murine macrophage responses to IFNγ. *Mycobacterium tuberculosis* utilizes at least two mechanisms to block responses to IFNγ. One is initiated by lipoproteins, acting through Toll-like receptor 2 (TLR2) and myeloid differentiation factor 88 (MyD88), while the other is initiated by mycobacterial peptidoglycan, acting in a TLR2- and MyD88-independent fashion.

To understand the contributions of *Mycobacterium tuberculosis* lipoproteins and TLR2 signaling to pathogenesis and immune evasion, a modified *Mycobacterium tuberculosis* strain (a ΔlspA strain) which is incapable of processing pre-lipoproteins to mature, triacylated lipoproteins was constructed. See the Example, infra. When examined for ability to serve as agonists for human TLR2, using an HEK293 cell line stably transfected with cDNA encoding human TLR2, the ΔlspA strain exhibited no more than 2% of the TLR2 agonist activity as compared to wild-type *Mycobacterium tuberculosis*. The ΔlspA strain also induced less TNFα secretion by macrophages during early hours of infection. These data indicate that lipoprotein processing is important for the TLR2 agonist activity of *Mycobacterium tuberculosis* and that lipoproteins are responsible for at least a potion of the proinflammatory stimulation of macrophages. However, the difference in TNFα secretion by macrophages infected with the ΔlspA strain versus the wild-type strain became insignificant after an extended period of time. When measured by the induction of MHC class II surface expression, the ΔlspA strain inhibited macrophage responses to IFNγ to the same extent as wild-type *Mycobacterium tuberculosis*. Moreover, macrophages lacking TLR2 appeared to be more resistant to inhibition by either strain of *Mycobacterium tuberculosis*. These results indicate that non-lipoprotein TLR2 agonists contribute to the inhibition of macrophage responses to IFNγ and that *Mycobacterium tuberculosis* utilizes nonlipoprotein- and non-TLR2-mechanisms to evade immune responses.

Indeed, phosphatidylinositol mannan from *Mycobacterium tuberculosis* inhibits macrophage responses to IFNγ. *Mycobacterium tuberculosis* inhibition of macrophage response to IFNγ also requires new protein synthesis, indicating that a late effect of innate immune stimulation is the inhibition of responses to IFNγ. These results further establish that *Mycobacterium tuberculosis* possesses multiple mechanisms of inhibiting responses to IFNγ.

The present invention features modified *Mycobacterium tuberculosis* strains which have at least one of these immune system evasion mechanisms inactivated or otherwise impaired. In many embodiments, the modified strains of the present invention lack a functional lspA gene. This can be achieved by deletion of the lspA gene. This can also be achieved by disrupting the lspA gene with one or more heterologous genes (e.g., one or more antibiotic-resistance genes or selection marker genes). Other modifications can also be used to inactivate the lspA gene. These modifications can be at the transcription level (e.g., by inactivating or disrupting the promoter or other 5' or 3' untranslated regulatory sequences), or at the translation level (e.g., by introducing stop codons, missense mutations, frame-shifting mutations, or other insertions or deletions that would disrupt the function of the encoded lipoprotein signal peptidase). Methods suitable for deleting or inactivating a gene in *Mycobacterium tuberculosis* include, but are not limited to, the homologous recombination method as described in the Example, infra, and the allelic exchange method as described in Sander et al., MOL. MICROBIOL. 52:1543-1552 (2004), which is hereby incorporated by reference in its entirety. The lspA gene encodes a lipoprotein signal peptidase which is an integral membrane protein that removes signal peptides from prolipoproteins during lipoprotein biosynthesis. Deletion or inactivation of the gene blocks the final acylation and creation of the mature triacylated lipoproteins that can serve as TLR2 agonists.

In one embodiment, the modified *Mycobacterium tuberculosis* strains of the present invention are modified H37Rv or H37Ra strains. H37Rv and H37Ra have ATCC Accession Nos. 25618 and 25177, respectively. Both H37Rv and H37Ra strains are commercially available.

The present invention also features methods for identifying non-lspA genes that are involved in *Mycobacterium tuberculosis* evasion of the host's immune response (including *Myco-* bacterium tuberculosis proinflammatory stimulation of macrophages or inhibition of macrophage response to IFNγ). The genes thus identified can be deleted or inactivated, either individually or in combination with lspA or other genes. As non-limiting examples, these genes can be involved in lipoprotein or glycolipid processing or protein synthesis.

The identification of these non-lspA genes typically starts with a background *Mycobacterium tuberculosis* strain in which the lspA gene has already been deleted or otherwise inactivated. One or more non-lspA genes in this background strain can then be deleted or inactivated using any suitable method known in the art. This modified strain can be subsequently used to infect macrophages to determine if the inactivated non-lspA gene(s) is involved in the proinflammatory stimulation of macrophages or the inhibition of macrophage response to IFNγ. Non-limiting examples of macrophage cells suitable for this purpose include RAW264.7, WEHI-3, P388D1, PU5-1R, and J774. Macrophages prepared from bone marrow or peripheral blood can also be used. In some cases, wild-type *Mycobacterium tuberculosis* is used as the background strain for the deletion or inactivation of non-lspA genes.

Macrophage responses to a modified *Mycobacterium tuberculosis* strain of the present invention can be determined by a variety of methods. A change in the response level, as compared to a control level (e.g., the response level of macrophages treated with the background strain), is often indicative that the non-lspA gene(s) being inactivated contributes to *Mycobacterium tuberculosis* evasion of the host's immune response.

In one embodiment, the proinflammatory stimulation effect of a modified *Mycobacterium tuberculosis* strain of the present invention is detected by measuring the level of TNFα secreted by the infected macrophages. TNFα is a multifunctional proinflammatory cytokine, which is mainly secreted by macrophages. TNFα is involved in the regulation of a wide spectrum of biological processes including cell proliferation, differentiation, apoptosis, lipid metabolism, and coagulation. A reduction in the level of TNFα secretion by macrophages infected with a modified *Mycobacterium tuberculosis* strain of the present invention, as compared to a background strain (e.g., a ΔlspA strain in which the non-lspA gene(s) inactivated in the modified strain is still functional), is indicative that the non-lspA gene(s) contributes to *Mycobacterium tuberculosis* proinflammatory stimulation of macrophages.

In another embodiment, the effect of a modified *Mycobacterium tuberculosis* strain of the present invention on macrophage responses to IFNγ is determined by measuring MHC class II surface expression or CIITA mRNA level in the infected macrophages after being treated with IFNγ. Other indicators or effectors in the IFNγ signaling pathway can also be used to monitor the effect of a modified *Mycobacterium tuberculosis* strain on macrophage response to IFNγ. IFNγ is the major means by which T cells cause macrophage activation, increasing their ability to kill bacteria. IFNγ increases the microbicidal abilities of macrophages by inducing the expression of iNOS and gp91-phox, proteins that are important of nitric oxide and reactive oxygen intermediates, respectively. The activation of macrophages by IFNγ is important for the elimination of bacteria that replicate within the phagosomes of macrophages. IFNγ also promotes antigen presentation by upregulating the expression of MHC proteins as well as other proteins involved in antigen processing and presentation. Some of the IFNγ-responsive target genes are primary responses activated by STAT1. Other target genes appear to be secondary responses activated by the expression of IRF-1 or the transcription activator CIITA (e.g., MHC class II α and β chains). A reduction in macrophage response to IFNγ after infection with a modified *Mycobacterium tuberculosis* strain of the present invention, as compared to a background strain (e.g., a ΔlspA strain in which the non-lspA gene(s) inactivated in the modified strain is still functional), is indicative that the non-lspA gene(s) inactivated in the modified strain contributes to *Mycobacterium tuberculosis* inhibition of macrophage response to IFNγ.

In yet another embodiment, the effect of a modified *Mycobacterium tuberculosis* strain of the present invention on macrophages is determined by measuring the TLR2 activation level in the infected macrophages. TLR2 is a member of the Toll-like receptor (TLR) family which plays an important role in pathogen recognition and activation of innate immunity. TLRs are highly conserved from *Drosophila* to humans and share structural and functional similarities. They recognize pathogen-associated molecular patterns that are expressed on infectious agents, and mediate the production of cytokines necessary for the development of effective immunity. The various TLRs exhibit different patterns of expression. TLR2 is expressed most abundantly in peripheral blood leukocytes, and mediates host response to Gram-positive bacteria and yeast via stimulation of NF-κB. Methods suitable for the detection of TLR2 or NF-κB activation are well known in the art. A reduction in the TLR2 activation level in macrophages that are infected with a modified *Mycobacterium tuberculosis* strain of the present invention, as compared to a background strain (e.g., a ΔlspA strain in which the non-lspA gene(s) inactivated in the modified strain is still functional), indicates that the non-lspA gene(s) inactivated in the modified strain contributes to the activation of TLR2 in the infected macrophages.

The effect of a modified *Mycobacterium tuberculosis* strain of the present invention on infected macrophages can be measured at any appropriate time after infection. For example, the effect can be measured at about 1, 2, 3, 4, 5, 6, 7, 8, 9, 10, 11, 12, 13, 14, 15, 16, 17, 18, 19, 20, 21, 22, 23, or 24 hours after infection. Suitable indicators for the effect include, but are not limited to, the TNFα secretion level, the MHC class II surface expression or CIITA mRNA level in response to IFNγ treatment, and the TLR2 activation level.

The present invention also features vaccine formulations comprising modified *Mycobacterium tuberculosis* strains of the present invention, and methods of using these vaccines for the treatment or prevention of *Mycobacterium tuberculosis* infection in mammals. Preferably, the modified *Mycobacterium tuberculosis* strains employed lack a functional lspA gene (e.g., by deletion, allelic substitution, or disruption by heterogonous gene or genes). More preferably, the modified *Mycobacterium tuberculosis* strains employed comprise deletion or inactivation of both the lspA gene and one or more non-lspA genes that are involved in *Mycobacterium tuberculosis* proinflammatory stimulation of macrophages or inhibition of macrophage response to IFNγ. A modified strain employed in a vaccine formulation of the present invention can also include deletion of other region or regions that are known to be involved in the attenuation in virulence, such as the RD1 region. A vaccine formation of the present invention can include two or more different *Mycobacterium tuberculosis* strains, each of which has different deletion or gene inactivation.

In many embodiments, a vaccine formulation of the present invention comprises one or more modified *Mycobacterium tuberculosis* strains of the present invention that are attenuated in virulence but are capable of sustaining viability and growth in a mammalian host. This provides a sustained exposure of the host's immune system to the avirulent *Myco-* bacterium tuberculosis strain(s), thereby eliciting an effective immune response against virulent *Mycobacterium tuberculosis* strains. The ability to sustain infection can be measured without undue experimentation by a number of ways described in the art. With the modified *Mycobacterium tuberculosis* strains of the present invention, one way of measuring sustained infection is by determining whether viable mycobacteria of the inoculated strain will remain resident in an immunocompetent mouse (e.g., BALB/c or C57BL/6 strain) for more than four weeks. Preferably, the inoculated mycobacteria will remain resident in the mouse for at least ten weeks. In one embodiment, viable mycobacteria of the inoculated strain will remain resident in the mouse for at least 20 weeks.

A vaccine formulation of the present invention is capable of protecting a mammal (e.g., human) from challenge by a virulent *M. tuberculosis* complex mycobacteria. This ability can be determined by a number of ways provided in the literature. As a non-limiting example, one method is aerogenically treating an immunocompetent mouse with the virulent mycobacteria. Aerogenic challenge is used because it closely mimics natural infection. The skilled artisan would understand that the ability of an avirulent mycobacterium to protect a mouse from challenge from a virulent mycobacterium is indicative of the ability of the avirulent mycobacterium to protect a human, including a human child, from tuberculosis infection. A more stringent test of an avirulent mycobacterium to prevent infection by a virulent challenge is to use an immunocompromised mammal such as a SCID mouse.

A vaccine formulation of the present invention can be administered in the form of a solid, liquid, or aerosol. Examples of solid compositions include pills, creams, and implantable dosage units. Pills can be administered orally. Therapeutic (including prophylactic) creams can be administered topically. Implantable dosage units can be administered locally, for example, in the lungs, or may be implanted for systematic release of the therapeutic composition, for example, subcutaneously. Examples of liquid compositions include formulations adapted for injection intramuscularly, subcutaneously, intravenously, intra-arterially, and formulations for topical (transdermal) and intraocular administration. Examples of aerosol formulations include inhaler formulations for administration to the lungs.

A vaccine formulation of the present invention typically includes a pharmaceutical carrier or excipient in which a modified *Mycobacterium tuberculosis* strain(s) of the present invention is suspended or dissolved. The carrier is non-toxic to the inoculated subject and compatible with the microorganism. Suitable pharmaceutical carriers include, but are not limited to, liquid carriers, such as normal saline and other non-toxic salts at or near physiological concentrations, and solid carriers, such as talc or sucrose. Gelatin capsules can serve as carriers for lyophilized vaccines. Adjuvants can be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, REMINGTON'S PHARMACEUTICAL SCIENCES (Gennaro, ed., 17th edition, Mack Publishing Co., Easton, Pa., 1985).

A vaccine formulation of the present invention can be administered by standard routes of administration. In general, a vaccine formulation can be administered by topical, oral, rectal, nasal, pulmonary, or parenteral (for example, intravenous, subcutaneous, or intramuscular) routes. In addition, a vaccine can be incorporated into sustained release matrices such as biodegradable polymers, the polymers being implanted in the vicinity of where delivery is desired, for example, at the site of a lesion. The method includes administration of a single dose, administration of repeated doses at predetermined time intervals, and sustained administration for a predetermined period of time.

A sustained release matrix is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The dosage of a vaccine composition will depend on the condition being treated, the particular composition used, and other clinical factors such as weight and condition of the patient, and the route of administration. In one embodiment, one dosage of the vaccine formulation includes about 1-2× $10^6$ colony forming units (CFU) of a modified *Mycobacterium tuberculosis* strain of the present invention. Multiple dosages can be used as needed to provide the desired level of protection from challenge.

The vaccine formulations of the present invention can be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing treatment of AIDS may benefit from the therapeutic methods and compositions described herein.

The present invention further features methods for identifying constituents or components of *Mycobacterium tuberculosis* that are TLR2 agonists or capable of inhibiting macrophage response to IFNγ. These method comprise:

providing a modified *Mycobacterium tuberculosis* strain lacking a functional lspA gene;

isolating a constituent or component of the modified strain;

treating or contacting macrophages with the isolated constituent/component; and detecting the IFNγ response level (or the TNFα secretion level or the TLR2 activation level) of the treated macrophages.

A reduction in the IFNγ response level after the treatment, as compared to that before the treatment, indicates that the isolated constituent/component is capable of inhibiting macrophage response to IFNγ. Likewise, an increase in the TNFα secretion level (or the TLR2 activation level) after the treatment, as compared to that before the treatment, is suggestive that the isolated constituent/component is a proinflammatory agonist (or a TLR2 agonist).

As a non-limiting example, a *Mycobacterium tuberculosis* constituent thus identified can be a protein, a glycolipid, a prolipoprotein, a polysaccharide, or a fragment or mixture thereof. A *Mycobacterium tuberculosis* constituent thus identified can also be, without limitation, a fragment of the cell wall, cell membrane or another cellular organelle, a fraction of a bacterial extract, or a mixture thereof. As used herein, a constituent is isolated if it is separated from its natural environment, such as by extraction, centrifugation, chromatography, electrophoresis, dialysis, filtration, or other separation or fractionation techniques, as appreciated by those skilled in the art.

The constituents/components thus identified can be used to identify lipoprotein-independent mechanisms that are involved in *Mycobacterium tuberculosis* proinflammatory stimulation of macrophages or inhibition of macrophage response to IFNγ. These constituents/components can also be used to identify inhibitors capable of reducing tuberculosis proinflammatory stimulation of macrophages or inhibition of macrophage response to IFNγ. Non-limiting examples of these inhibitors include antibodies that can specifically bind to these constituents/components and therefore neutralize their effects on macrophages. Suitable antibodies include, but are not limited to, polyclonal antibodies, monoclonal antibodies, Fab fragments, $F(ab')_2$ fragments, Fv fragments, single chain Fv fragments, diabodies, minibodies, scFv-Fc, chimeric antibodies, humanized antibodies, and human antibodies.

The present invention also features methods for identifying agents capable of reducing *Mycobacterium tuberculosis* proinflammatory stimulation of macrophages or inhibition of macrophage response to IFNγ. These methods comprise:
    providing a modified *Mycobacterium tuberculosis* strain which lacks a functional lspA gene;
    contacting macrophages with said modified strain in the presence of an agent of interest; and
    detecting the IFNγ response level (or the TNFα secretion level) of the macrophages after the contact.

An increase in the IFNγ response level (or a reduction in the TNFα secretion level), as compared to a control level (e.g., that measured in the absence of the agent of interest), is indicative that the agent of interest can reduce *Mycobacterium tuberculosis* inhibition of macrophage response to IFNγ (or *Mycobacterium tuberculosis* proinflammatory stimulation of macrophages). Preferably, an agent thus identified can reduce *Mycobacterium tuberculosis* proinflammatory stimulation of macrophage or inhibition of macrophage response to IFNγ by at least 20%, 30%, 40%, 50%, 60%, 70%, 80%, 90%, or 100%.

The present invention further features pharmaceutical compositions comprising the agents thus identified, and methods of using the agents for the treatment or prevention of *Mycobacterium tuberculosis* infection in mammals. A pharmaceutical composition of the present invention typically includes a therapeutically (including prophylactically) effective amount of an agent identified by the present invention and a pharmaceutically acceptable carrier. Suitable pharmaceutically acceptable carriers include solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, that are compatible with pharmaceutical administration. The use of such media and agents for pharmaceutically active substances is well-known in the art. Supplementary agents can also be incorporated into the composition. A pharmaceutical composition of the present invention can be formulated to be compatible with its intended route of administration.

A pharmaceutical composition of the present invention can be administered to a patient or mammal in a desired dosage. A suitable dosage may range, for example, from 5 mg to 100 mg, from 15 mg to 85 mg, from 30 mg to 70 mg, or from 40 mg to 60 mg. Dosages below 5 mg or above 100 mg can also be used. The pharmaceutical composition can be administered in one dose or multiple doses. The doses can be administered at intervals such as once daily, once weekly, or once monthly.

Toxicity and therapeutic efficacy of an agent identified according to the present invention can be determined by standard pharmaceutical procedures in cell culture or experimental animal models. For instance, the LD50 (the dose lethal to 50% of the population) and the ED50 (the dose therapeutically effective in 50% of the population) can be determined. The dose ratio between toxic and therapeutic effects is the therapeutic index, and can be expressed as the ratio LD50/ED50. In many cases, agents that exhibit large therapeutic indices are selected.

In addition, the present invention features methods for isolating *Mycobacterium tuberculosis* components for adjuvant therapy. These methods do not require removal of lipoproteins. The methods typically comprise:
    disrupting a *Mycobacterium tuberculosis* strain which lack a functional lspA gene;
    fractionating the components of the strain; and
    isolating one or more cell wall components for adjuvant therapy.

In one embodiment, the cell wall component(s) is isolated by extraction. The isolation may or may not involve chemical or enzymatic cleavage(s).

This invention is further illustrated by the following example, which is not to be construed in any way as imposing limitations upon the scope of the present invention. Various changes and modifications within the scope of the present invention will become apparent to those skilled in the art from the present description.

The following example examined whether lipoprotein-mediated inhibition is dominant in the context of intact *Mycobacterium tuberculosis*. As demonstrated by the example, the disruption of the *Mycobacterium tuberculosis* lipoprotein signal peptidase (lspA) resulted in loss of mature lipoproteins and lipoprotein TLR2 agonist activity, but had no effect on the mutant strain's ability to inhibit macrophage responses to IFNγ. The disruption of TLR2 on macrophages, however, significantly reduced the cells' sensitivity to inhibition by live *Mycobacterium tuberculosis* and *Mycobacterium tuberculosis* lysates.

EXAMPLE

A. Materials and Methods

The following materials and methods were employed throughout this Example.

Bacteria and TLR2 Agonists

All *Mycobacterium tuberculosis* strains were grown in shaking cultures to mid-log phase in Middlebrook 7H9 broth (Difco) supplemented with 0.2% glycerol, 10% OADC, and 0.05% Tween 80. *Mycobacterium tuberculosis* cultures used for infection of macrophages were grown the same medium with low-endotoxin ADC (dextrose, catalase and cell culture tested BSA, all from Sigma) substituted for OADC. This media contained less than 1 endotoxin unit per ml. γ-irradiated *Mycobacterium tuberculosis* H37Rv (Colorado State University, Fort Collins, Colo., NIH, NIAID Contract N01 AI-75320) was prepared as described in Kincaid and Ernst, J. IMMUNOL. 171:2042-2049 (2003), which is hereby incorporated by reference in its entirety. Phosphatidylinositol mannan$_{1+2}$ (PIM, Colorado State University) was stored at 1 mg/ml in DMSO (Sigma) at −80° C. (S)-[2,3-Bis(palmitoyloxy)-(2-RS)-propyl]-N-palmitoyl-(R)-Cys-(S)-Ser-(S)-Lys$_4$-OH, 3HCl (Pam$_3$CSK$_4$, Calbiochem) and (S)-[2,3-Bis (palmitoyloxy)-(2-RS)-propyl]-(R)-Cys-(S)-Ser-(S)-Lys$_4$×3 CF3COOH (Pam$_2$CSK$_4$, InvivoGen) were stored at 1 mg/ml in endotoxin-tested water (Gibco) at −80° C.

Mice

C57BL/6, IL6$^{-/-}$ and TLR2$^{-/-}$ mice were obtained from The Jackson Laboratory (Bar Harbor, Me.) and maintained under specific pathogen-free conditions. TLR2$^{-/-}$ mice from The Jackson Laboratory have been backcrossed onto the C57BL/6 background for 9 generations. All work with animals was approved by the NYU School of Medicine Institutional Animal Care and Use Committee.

Cell Lines

RAW264.7 and HEK-293 cells (American Type Culture Collection, Manassas, Va.) were grown in DMEM with 10% heat inactivated FCS and 2 mM L-Glutamine (all from Gibco). HEK 293-TLR2 cells were provided by Dr. Douglas Golenbock (University of Massachusetts), and were grown in the same medium with 500 μg/ml Geneticin (Gibco). Cells were allowed to adhere overnight before *Mycobacterium tuberculosis* treatment or infection. L929 cells (ATCC) were maintained in DMEM with 10% FCS, 2 mM L-glutamine, 100 μM nonessential amino acids, and 55 μM β-mercaptoethanol (Gibco). L cell-conditioned medium was collected from confluent L929 cultures and stored at −20° C.

LspA Knockout and Complement

A lspA knockout mutant was created with the conditionally replicating mycobacteriophage as described in Bardarov et al., MICROBIOLOGY 148:3007-3017 (2002), which is hereby incorporated by reference in its entirety. The upper (886 bp) and lower (1125 bp) allelic exchange substrates (AES) were PCR amplified (for complete list of primers see Table 1) from H37Rv genomic DNA and ligated into pCR2.1-TOPO (Invitrogen). The AES were sequenced and subcloned into pYUB854. Following transduction of H37Rv and plating on Middlebrook 7H9 agar with ADC and hygromycin (50 μg/ml), 6 colonies were picked and screened for the absence of lspA transcript by real-time RT-PCR. A PCR fragment encoding the entire lspA ORF and the preceding 470 bp was ligated into pMV306 (Stover et al., NATURE 351:456-460 (1991), which is hereby incorporated by reference in its entirety) for complementation of the lspA mutant. Transformed bacteria were plated on Middlebrook 7H9 agar supplemented with ADC and 25 μg/ml of kanamycin and 4 colonies were picked and analyzed for complementation by real-time RT-PCR.

TABLE 1

Primer Sets Used in the Examples

| Target | Forward | Reverse |
|---|---|---|
| Allelic Exchange Substrate | | |
| Upper | SEQ ID NO: 1 | SEQ ID NO: 2 |
| Lower Complement | SEQ ID NO: 3 | SEQ ID NO: 4 |
| lspA | SEQ ID NO: 5 | SEQ ID NO: 6 |
| Quantitative Reverse Transcription-PCR | | |
| lspA reverse transcription | | SEQ ID NO: 7 |
| lspA | SEQ ID NO: 8 | SEQ ID NO: 9 |
| murine CIITA (all forms) | SEQ ID NO: 10 | SEQ ID NO: 11 |
| murine GAPDH | SEQ ID NO: 12 | SEQ ID NO: 13 |

Western Blotting

Protein extraction was performed according to the protocol described in MOLECULAR GENETICS OF MYCOBACTERIA (Hatfull and Jacobs, eds. 2000, ASM Press, Washington, D.C.), which is hereby incorporated by reference in its entirety. Briefly, 2 ml of bacterial culture at mid-log phase was sedimented and washed once with 2 ml of PBS and resuspended in 300 μl of extraction buffer (50 mM Tris-HCl pH 7.5, 5 mM EDTA, 0.6% SDS, 10 mM NaPO4, and Roche Complete Protease Inhibitor Cocktail) and added to 0.2 ml of 0.1 mm zirconia/silica beads. The tube was vortexed for 5 min and subsequently sedimented for 2 min at 12600×g. The supernatant was removed and the protein concentration determined with the BCA protein assay kit (Pierce). 0.2-1.5 μg was separated on a 10% SDS-PAGE gel and immunoblotting was performed as described in Kincaid and Ernst, supra. Polyclonal anti-MPT83 was provided by Dr. Harald Gotten Wiker (Gades Institutt, Norway) and incubated overnight at 4° C. at a dilution of 1:2000.

Infection of Cell Monolayers

Bacteria from mid-log cultures ($A_{580}$~0.5) were sedimented, resuspended in cell culture media, vortexed for 3 minutes in O-ring tubes containing two 5 mm glass beads (Fisher) and passed through a 5 μm sterile filter (Millipore). Bacteria were enumerated in a Petroff-Hausser chamber and also serially diluted and plated on Middlebrook 7H10 and 7H9/ADC agar plates.

Bacterial Lysates for Cell Stimulation

Mid-log cultures of *Mycobacterium tuberculosis* grown in low endotoxin media were sedimented, washed once with PBS, and resuspended in 1 ml of extraction buffer or PBS with or without protease inhibitors. Bacteria were disrupted in O-ring tubes containing 0.5 ml of 0.1 mm zirconia/silica beads and mechanically disrupted with three 1 min pulses at maximum speed in a BioSpec Products BeadBeater™ with 3 min intervals on ice. The lysates were sedimented for 1 min at 12600×g and the supernatants were transferred and the efficacy of disruption was assayed as soluble protein concentration (BCA protein assay kit; Pierce) and enumeration of viable bacteria before and after bead beating. Equivalent amounts of protein (~0.8 μg per 1×10$^6$ cfu) were released from all three strains upon bead beating, indicating a comparable efficiency of lysis. Furthermore, a 10$^4$ fold difference was seen in the number of viable bacteria before and after beadbeating of H37Rv.

Isolation and Culture of Bone Marrow-Derived Macrophages (BMDM)

Bone marrow cells were isolated as described in Nagabhushanam et al., J. IMMUNOL. 171:4750-4757 (2003), which is hereby incorporated by reference in its entirety. Erythrocytes were lysed using ACK lysis buffer (155 mM ammonium chloride, 10 mM potassium bicarbonate, 100 μM EDTA, pH 7.4, all from Sigma). Cells were plated in 150×25-mm bacterial grade petri dishes (Falcon) at 3-4×10$^6$/plate, in DMEM with 10% FCS, 20% L929-cell conditioned medium, 1 mM sodium pyruvate, 2 mM L-glutamine and 100 U/ml Penicillin/100 μg/ml streptomycin sulfate (Gibco). The cells were incubated at 37° C. in 5% CO$_2$ for 3 days, after which the medium was replaced. Adherent cells were harvested between days 6 and 10; the cells were incubated in ice cold Dulbecco's PBS (DPBS) containing 5 mM EDTA for 20 minutes, detached from the plates by vigorous pipetting, then washed and replated at 5×10$^5$/well in 12-well tissue culture plates in DMEM supplemented with 10% FCS, 10% L929-cell conditioned medium, 1 mM sodium pyruvate and 2 mM L-glutamine.

Flow Cytometry

Following infection with live *Mycobacterium tuberculosis* or treatment with PIM or $Pam_3CSK_4$, RAW264.7 cells were treated with 20 ng/ml recombinant murine IFNγ (400-4000 U/ml, BD Pharmingen). Cells were rinsed with DPBS and incubated for 10 min in DPBS containing 1 mM EDTA. Cells were then scraped, washed, and stained with PE conjugated anti-mouse I-A/I-E (BD Pharmingen). For experiments with live *Mycobacterium tuberculosis*, cells were fixed overnight with 1% paraformaldehyde (Sigma). Cells were analyzed on a FACSCalibur (Becton Dickinson, 10,000 total events gated by forward and side scatter).

mRNA Quantitation

For experiments with $Pam_3CSK_4$, total RNA was harvested using Qiagen RNeasy columns. For *Mycobacterium tuberculosis* cultures and cells infected with live *Mycobacterium tuberculosis* or treated with *Mycobacterium tuberculosis* whole cell lysates, total RNA was harvested using Trizol Reagent (Invitrogen). DNA was removed using DNA-free (Ambion). Total RNA was quantitated using RiboGreen (Molecular Probes). Ten ng of bacterial or one µg of mammalian RNA was reverse transcribed using the Reverse Transcription System (Promega). For mammalian RNA, reverse transcription was primed with random hexamers and oligo(dT). For bacterial RNA, reverse transcription was primed with gene-specific primers (listed in Table 1). The cDNA equivalent of 0.2 ng of total bacterial RNA or 10 ng of total mammalian RNA (50 ng for CIITA) was analyzed by quantitative PCR using Platinum SYBR Green qPCR SuperMix UDG (Invitrogen) on an MJ Research Opticon 2 (for primers, see Table 1). For quantitation, the relative values were determined by comparing the threshold cycle of each sample to a standard curve consisting of serial dilutions of a positive control cDNA sample.

ELISA

Cell supernatants for ELISA were harvested after the indicated time, and were stored at −80° C. ELISAs were performed with optimized antibody sets specific for human IL-8 (BD Pharmingen) or murine TNFα (eBiosciences), used according to the manufacturers' directions. Samples were diluted 1:10, 1:100 or 1:1000 to allow detection within the range of each assay. Results for experiments with live or lysed *Mycobacterium tuberculosis* H37Rv were quantitated using a SpectraMax $340PC^{384}$ spectrophotometer, and all other results were quantitated using an $EL_x800_{UV}$ spectrophotometer (Bio-Tek Instruments, Inc).

Inhibition of Protein Synthesis

Cells were pretreated with cycloheximide (Calbiochem) or solvent control (0.02% ethanol, Sigma) for 1 hour before addition of *Mycobacterium tuberculosis* whole cell lysates. After 8 hours, media was removed and stored at −80° for ELISA and cytotoxicity assays. Cells were treated with IFNγ or left untreated for 4 hours and RNA was harvested as described above.

B. Results $Pam_3CSK_4$, a Synthetic Lipoprotein Unrelated to the *Mycobacterium Tuberculosis* 19 kDa Lipoprotein, is a Potent Inhibitor of Macrophage Responses to IFNγ

It has been found that the *Mycobacterium tuberculosis* 19 kDa lipoprotein inhibits macrophage responses to IFNγ and that this inhibition is dependent on TLR2 and MyD88. Although considerable attention has been focused on the properties of the *Mycobacterium tuberculosis* 19 kDa lipoprotein, this lipoprotein is unlikely to be the sole mediator of *Mycobacterium tuberculosis* inhibition of macrophages. Not only is the 19 kDa lipoprotein not required for *M. bovis* bacille Calmette-Guerin (BCG) inhibition of IFNγ-dependent antigen processing in infected macrophages, at least one other *Mycobacterium tuberculosis* lipoprotein is capable of causing this inhibition.

It has also been reported that in addition to native, full-length 19 kDa lipoprotein, a synthetic triacylated hexapeptide containing the N-terminal 6 amino acid residues of the 19 kDa lipoprotein can also inhibit macrophage responses to IFNγ. To determine if treatment with an unrelated lipopeptide could reproduce this inhibition, $Pam_3CSK_4$ was examined. $Pam_3CSK_4$ is a triacylated hexapeptide that has no peptide sequence identity with any *Mycobacterium tuberculosis* open reading frame, as determined by BLASTP search (Altschul et al., NUCLEIC ACIDS RES. 25:3389-3402 (1997), which is hereby incorporated by reference in its entirety) of all non-redundant GenBank coding sequences of *Mycobacterium tuberculosis*. Treatment of RAW264.7 cells with $Pam_3CSK_4$ profoundly inhibited IFNγ induction of MHC class II surface expression; as little as 1 nM $Pam_3CSK_4$ caused greater than 90% inhibition of IFNγ induction of surface MHC class II (FIG. 1). IFNγ induction of class II transactivator (CIITA) mRNA was also potently inhibited in $Pam_3CSK_4$ treated cells and this inhibition was likely responsible for the defect in MHC class II surface expression. These findings are consistent with the inhibitory effects of higher (micromolar) concentrations of synthetic bacterial lipopeptides on responses to IFNγ.

Construction and Characterization of LspA Mutant

The finding that a synthetic lipoprotein unrelated to the 19 kDa lipoprotein is a potent inhibitor of IFNγ suggests that other *Mycobacterium tuberculosis* lipoproteins could contribute to inhibition of macrophages via TLR2. Bioinformatic analysis of the *Mycobacterium tuberculosis* genome revealed 99 putative lipoproteins, accounting for approximately 2.5% of its proteome. Given the number and variety of lipoproteins and the evidence that the TLR2 agonist activity is attributable to the triacylated amino terminus rather than other protein domains, deletion of any single lipoprotein might not render *Mycobacterium tuberculosis* unable to inhibit macrophage responses to IFNγ. To evaluate the global role of mature lipoproteins in the modulation of macrophage responses to IFNγ, experiments were carried out to disrupt the lspA gene which encodes prolipoprotein signal peptidase II, the enzyme that cleaves the signal sequence from diacylated prolipoproteins at a site directly preceding the lipidated cysteine residue. The exposure of the primary amine group on the newly exposed. N-terminal cysteine then allows for the final acylation and creation of the mature triacylated lipoproteins capable of serving as TLR2 agonists (FIG. 2A).

Figure 2A:
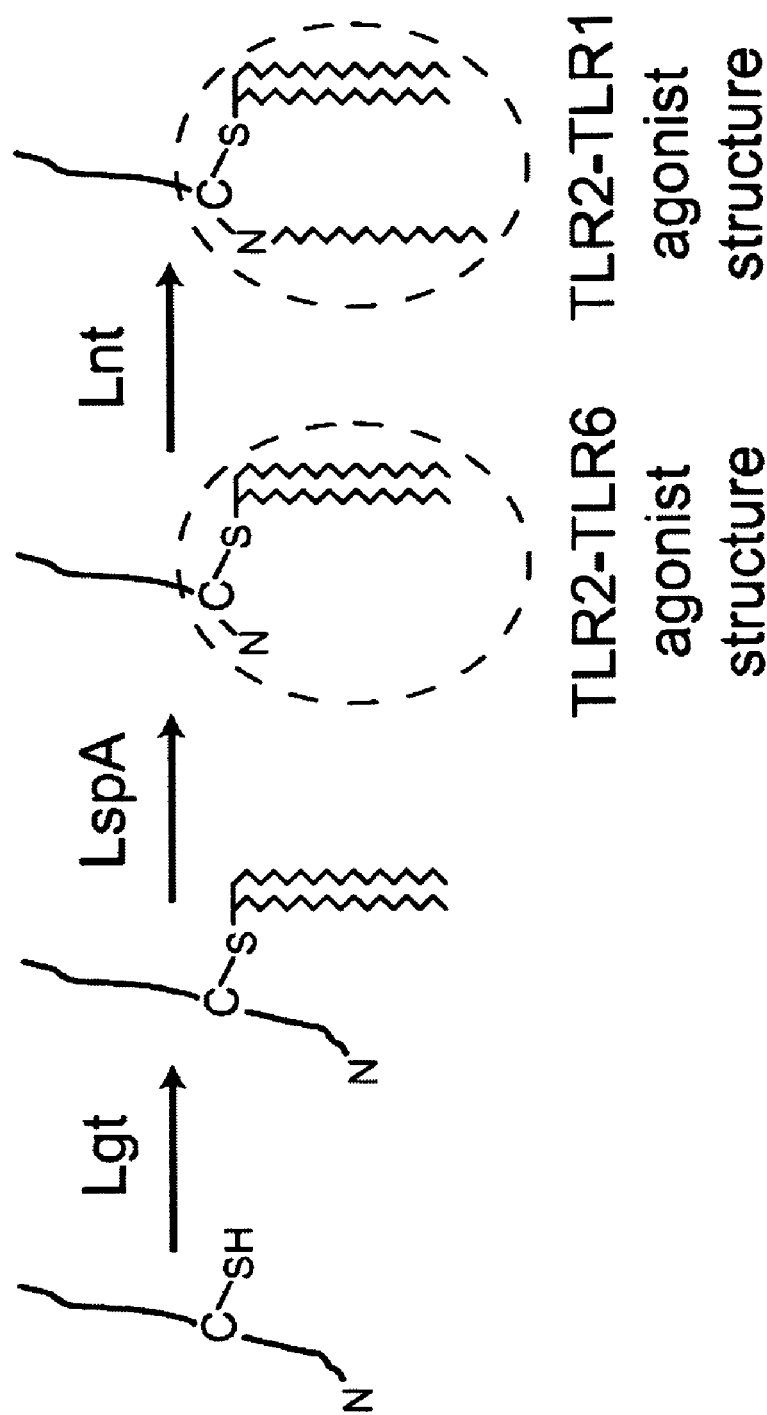
FIG. 2A diagrammatically illustrates bacterial lipoprotein processing. Nascent preprolipoproteins are translocated across the bacterial membrane where prolipoprotein diacylglycerol transferase (the product of lgt) catalyzes the addition of diacylglycerol to the sulfhydryl group of a cysteine-residue near the amino terminus and preceded by residues characteristic of a "lipobox." The signal peptide on diacylglycerol-modified prolipoprotein is cleaved on the amino-terminal side of the modified cysteine (by prelipoprotein signal peptidase II, the product of lspA.) The cleaved lipoprotein containing diacylglycerol can act as an agonist for TLR2/TLR6 heterodimers. Further addition of a fatty acid to the newly exposed free amine on the modified cysteine (by lipoprotein N-acyl transferase, the product of lnt) results in a triacylated lipoprotein that can act as an agonist for TLR2/TLR1 heterodimers.
Figure 2B:
FIG. 2B shows the genomic map of lspA and flanking genes in Mycobacterium tuberculosis H37Rv.
Figure 2C:
FIG. 2C depicts an allelic exchange substrate used to make a ΔlspA knockout mutant with the mycobacteriophage system. The shaded box with hyg cassette represents the region deleted from lspA.
Figure 2D:
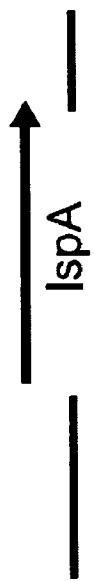
FIG. 2D shows a genomic fragment PCR amplified to create ΔlspAattB::lspA complement.
Figure 3A:
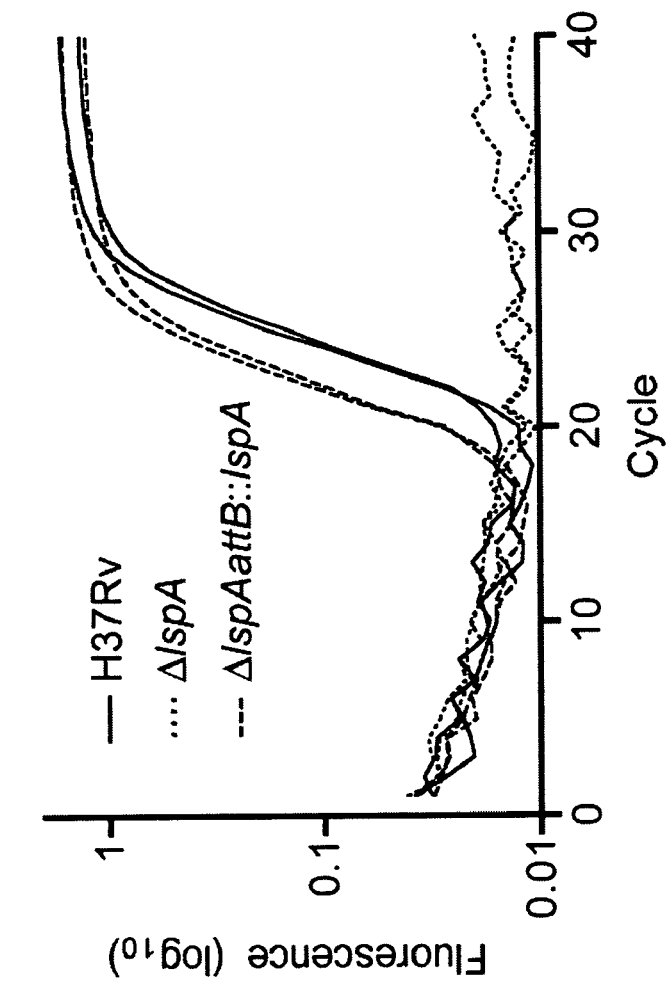
FIG. 3A demonstrates phenotypic confirmation of lspA mutant by real-time RT-PCR. Real-time RT-PCR results indicated the expression of lspA transcript in Mycobacterium tuberculosis H37Rv, ΔlspA (lspA mutant), and ΔlspAattB::lspA (lspA complement).
Figure 3B:
FIG. 3B illustrates phenotypic confirmation of lspA mutant by Western blot. Western immunoblot of bacterial extracts with anti-MPT83 antibody showed the migration of MPT83 from H37Rv, ΔlspA, and complement (attB::lspA), as indicated. The blot was loaded with 0.2 µg of total protein from the wild-type (H37Rv) and complemented mutant (attB::lspA) extract and 1.5 µg of total protein from the lspA mutant (ΔlspA), to demonstrate the mobility difference of the lspA mutant in the face of a lower abundance of Mpt83 in the mutant. Although MPT83 is present in lower abundance in the lspA mutant, the other two lipoproteins (19 and 38 kDa lipoproteins) analyzed are present in similar quantities in wild-type, lspA mutant, and complemented lspA mutant. Data shown is representative of 3 independent extractions.

Genomic search of the annotated *Mycobacterium tuberculosis* H37Rv genome sequence revealed a single copy of a putative lspA (FIG. 2A). A deletion mutant of lspA was created by homologous recombination using a specialized phage transduction system (FIG. 2B). The lspA mutant did not express detectable lspA mRNA and was unable to process MPT83, a well-characterized lipoprotein of *Mycobacterium tuberculosis* (FIG. 3). Complementation of the mutant with an integrating plasmid carrying lspA under the control of its native promoter restored prolipoprotein signal peptidase activity. These results indicate the presence of a single functional copy of lspA gene in H37Rv whose function is to cleave the signal peptide from prolipoproteins. Growth kinetics of the lspA mutant in rich broth medium (7H9 supplemented with OADC and glycerol) revealed a mild growth defect during the late-log phase (slopes, wild type 0.36 OD/24 h;

mutant 0.27) which corrected with complementation. The lspA mutant also reached stationary phase at a slightly lower bacterial density as compared to wild-type ($A_{580}$, wild type 2.0; mutant 1.8). On 7H9 solid agar, the mutant formed raised microcolonies with smoother borders compared to wild type, compatible with alteration of the cell surface.

Prolipoprotein Processing is Required for *Mycobacterium Tuberculosis* Activation of HEK293 Cells via TLR2

To characterize the role of prolipoprotein processing in generating *Mycobacterium tuberculosis* TLR2 agonist activity, the ability of wild-type *Mycobacterium tuberculosis* H37Rv, ΔlspA, and the ΔlspAattB::lspA complemented strain to stimulate HEK293 cells stably transfected to constitutively express human TLR2 (293-TLR2 cells) was examined. These cells produce IL-8 in response to IL-1β or lipopeptide TLR2 agonists (FIG. 8A).

Figure 4A:
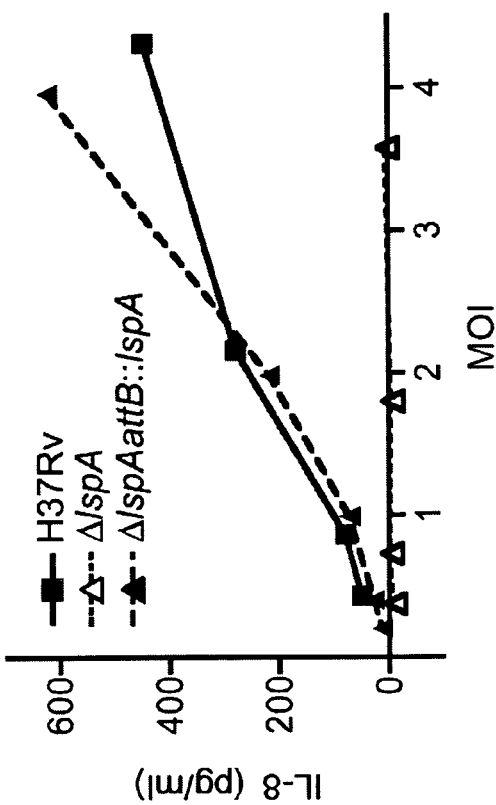
FIG. 4A indicates that prolipoprotein processing is required for Mycobacterium tuberculosis stimulation of HEK293 cells expressing TLR2. HEK293 cells expressing human TLR2 ("293-TLR2") were infected with wild type H37Rv (filled squares), ΔlspA (open triangles) or ΔlspAattB::lspA complement (filled triangles) at a range of multiplicities of infection, as indicated. Cell supernatants were harvested after 24 hours and secretion of IL-8 into the medium was quantitated by ELISA (mean of duplicate assays). Background level of IL-8 secreted into media of untreated cells (70.9 pg/ml) was subtracted from all values. Results are representative of 4 independent experiments. Because small changes in multiplicity of infection (MOI) led to significant changes in IL-8 secretion, all MOIs were confirmed by quantitative culture.

While wild type H37Rv induced 293-TLR2 cells to produce IL-8 in a dose-dependent manner, the response to ΔlspA bacteria was reduced by greater than 95% compared to that of wild-type H37Rv and the complemented strain (FIG. 4A). HEK293 cells that did not express TLR2 did not produce IL-8 upon treatment with any of the *Mycobacterium tuberculosis* strains tested.

Figure 4B:
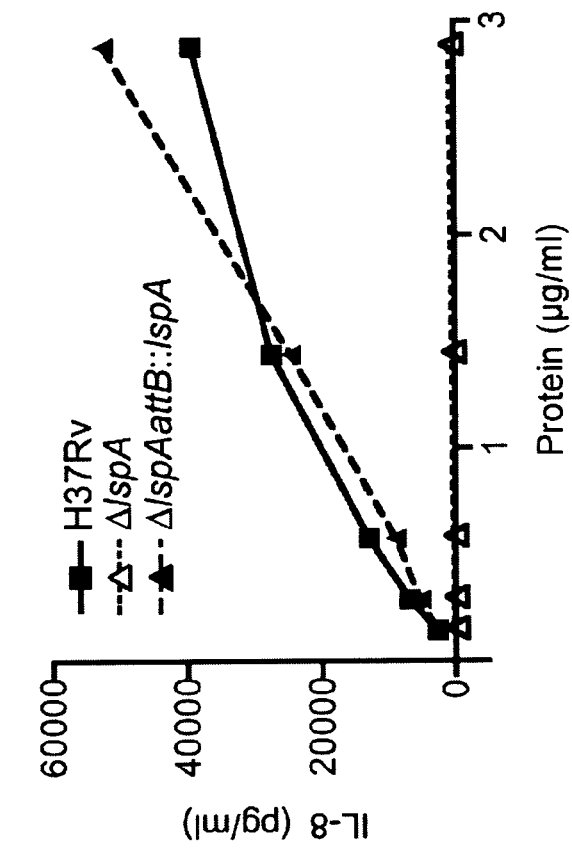
FIG. 4B shows another experiment demonstrating that prolipoprotein processing is required for Mycobacterium tuberculosis stimulation of 293-TLR2. 293-TLR2 cells were treated with whole cell lysates from wild type H37Rv, ΔlspA or ΔlspAattB::lspA complement at a range of dilutions, as indicated. Protein concentrations refer to soluble protein in whole cell lysates. Supernatants were analyzed as described for (FIG. 4A). Background level of IL-8 secreted into media of untreated cells (45.2 pg/ml) was subtracted from all values. Data is mean±SD of triplicate assays. Results are representative of 4 independent experiments.

Since HEK293 cells are not professional phagocytes and therefore, may only detect TLR2 agonists present on the surface of the bacteria, experiments were performed to determine if lipoprotein TLR2 agonists were present but not exposed on the surface of live ΔlspA bacteria. Treatment of 293-TLR2 cells with wild-type whole-bacteria lysates induced approximately 25 fold greater amounts of IL-8 than that seen with live bacteria, but lysis of the ΔlspA strain did not correct the defect in activation of 293-TLR2 cells observed with live bacteria: the amount of IL-8 secreted in response to lysates from ΔlspA bacteria was only 2% percent of that seen with lysates from wild-type bacteria (FIG. 4B). This finding indicates that the defect in stimulation of 293-TLR2 cells is not simply due to sequestration or mistrafficking of TLR-2 agonists in the ΔlspA mutant. Furthermore, expression of transfected CD14, a coreceptor for some TLR2 agonists, had only a minor effect on IL-8 secretion in response to lysates from the ΔlspA strain; in transfected cells, there was a greater than 90% decrease in the IL-8 secreted in response to the lspA mutant compared to the wild type strain.

Macrophage Activation by Lipoprotein and Nonlipoprotein Components in *Mycobacterium Tuberculosis*

Figure 5A:
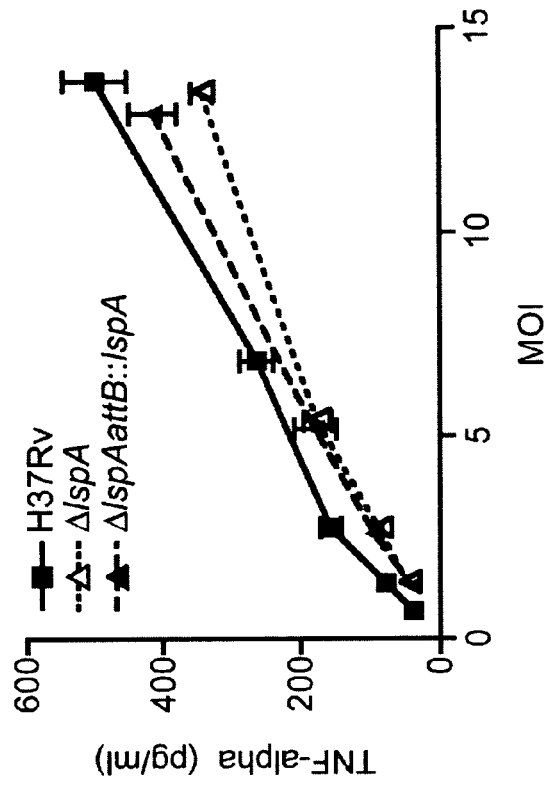
FIGS. 5A and 5B depict induction of macrophage TNFα secretion by lipoprotein and non-lipoprotein components of intact Mycobacterium tuberculosis.
Figure 5B:
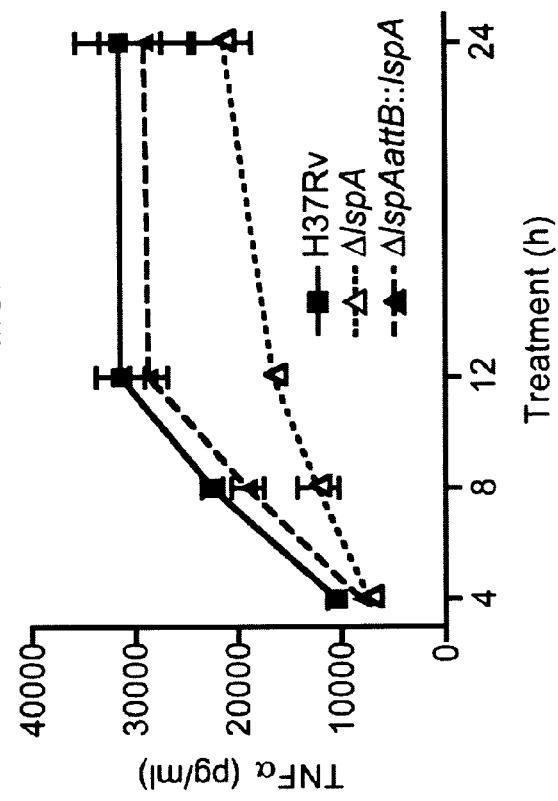

*Mycobacterium tuberculosis* has been reported to activate macrophages through TLR2 and TLR4, and through one or more MyD88-independent mechanisms. To determine the relative contributions of lipoprotein and nonlipoprotein proinflammatory agonist activities of *Mycobacterium tuberculosis*, RAW264.7 cells were infected with live wild-type H37Rv, ΔlspA, and the ΔlspAattB::lspA complement. At 8 h post infection, the lspA mutant stimulated RAW264.7 cells to secrete 20-30% less TNFα than RAW264.7 cells infected with wild-type bacteria at the same multiplicity of infection (MOI) (FIG. 5A). To compare TNFα secretion in response to wild type, ΔlspA and complemented strains at different times post-treatment, RAW264.7 cells were treated with whole cell lysates of the three strains for 4, 8, 12, and 24 h. After 8 and 12 h of treatment, significantly less TNFα was secreted by RAW264.7 cells treated with whole cell lysates from the ΔlspA strain than from the wild type or complemented strain (FIG. 5B). This difference persisted at the 24 h time point, but was no longer statistically significant. The partial response of RAW264.7 cells to the lspA mutant indicates that lipoproteins are responsible for a portion of the proinflammatory stimulation of macrophages in response to infection with live *Mycobacterium tuberculosis*. There remains, however, significant lipoprotein independent stimulation of macrophage TNFα secretion in response to *Mycobacterium tuberculosis*.

Lipoprotein-Independent Inhibition of the Macrophage Response to IFNγ

Figure 6:
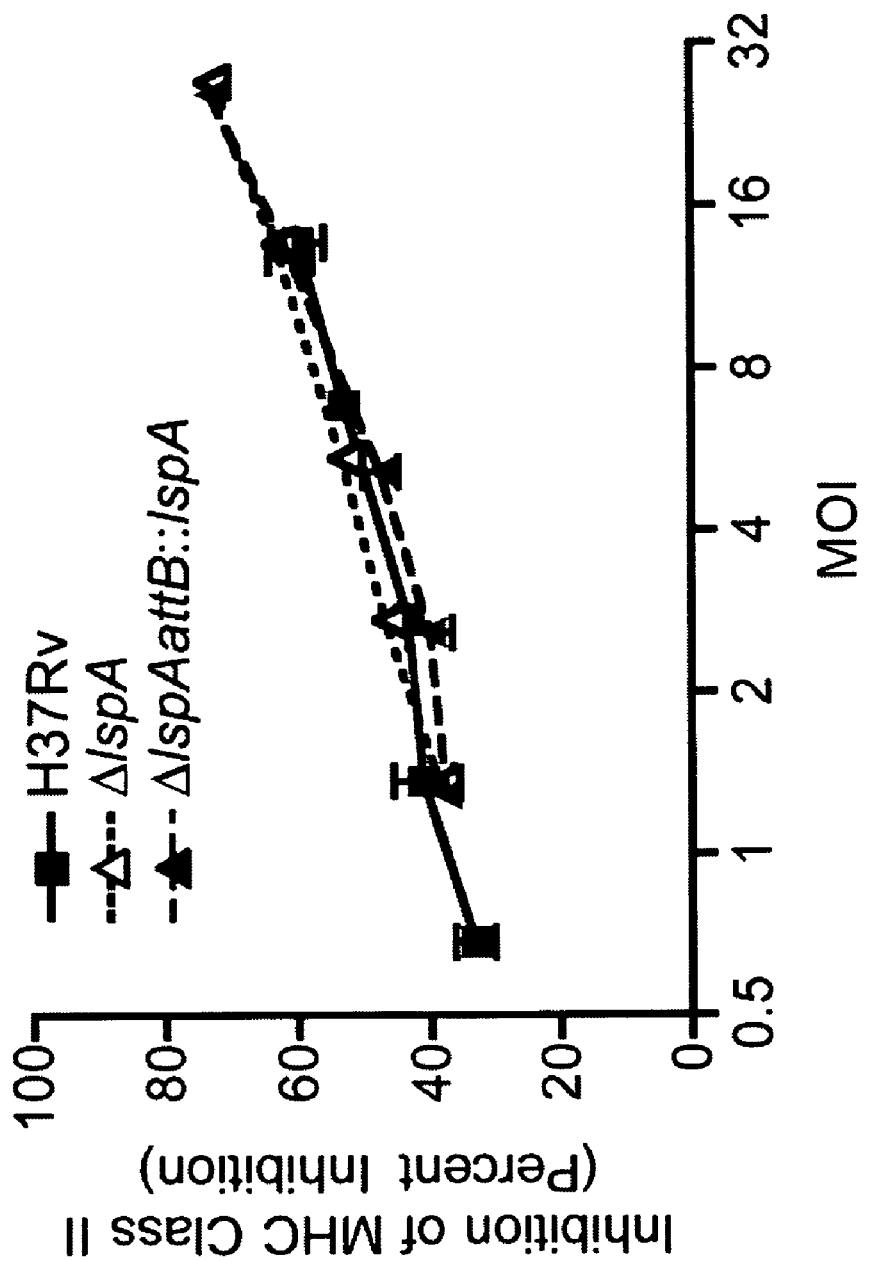
FIG. 6 illustrates lipoprotein-independent inhibition of the macrophage response to IFNγ. RAW264.7 cells were infected with wild type H37Rv (filled squares), ΔlspA (open triangles), or ΔlspAattB::lspA complement (filled triangles) at a range of multiplicities of infection, as indicated. After 8 h infection, cells were treated with IFNγ for 16-24 hours. Cells were stained with PE-conjugated anti-mouse I-A/I-E and analyzed by flow cytometry (10,000 events, gated by forward and side scatter, were counted). Values shown are mean fluorescent intensity (mean±SD of triplicate assays). Results are representative of 4 independent experiments.

To investigate the relative contribution of lipoproteins to *Mycobacterium tuberculosis* inhibition of macrophage responses to IFNγ, RAW264.7 cells were infected with wild-type H37Rv, ΔlspA, and the ΔlspAattB::lspA complement. This revealed no difference in the ability of the three strains to inhibit the induction of MHC class II surface expression in response to IFNγ at a wide range of MOI (FIG. 6). Similarly, no difference between wild-type H37Rv and ΔlspA in the inhibition of IFNγ induction of CIITA mRNA in infected RAW264.7 cells was observed. These results suggest that, although lipoproteins contribute to inhibition of macrophage responses to IFNγ, they are dispensable for the inhibition of macrophage responses to IFNγ by live *Mycobacterium tuberculosis*.

Figure 7A:
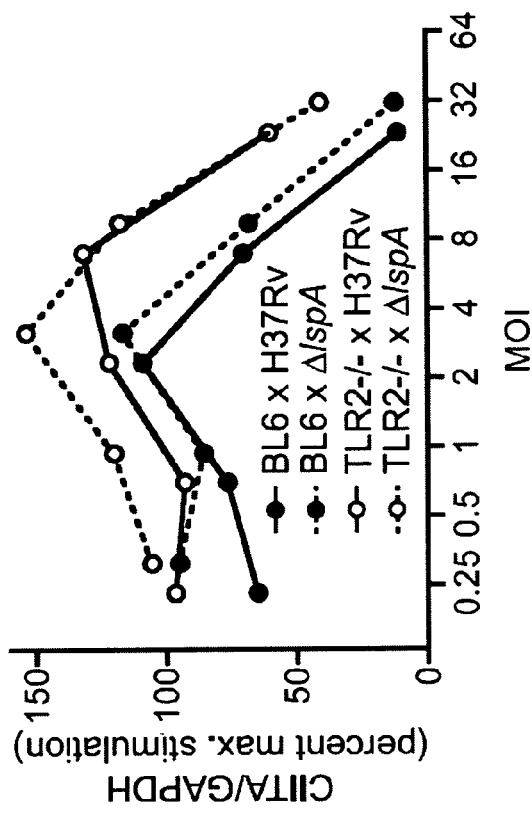
FIGS. 7A and 7B demonstrate that TLR2$^{-/-}$ macrophages are less sensitive than wild-type macrophages to Mycobacterium tuberculosis inhibition of response to IFNγ.
Figure 7B:
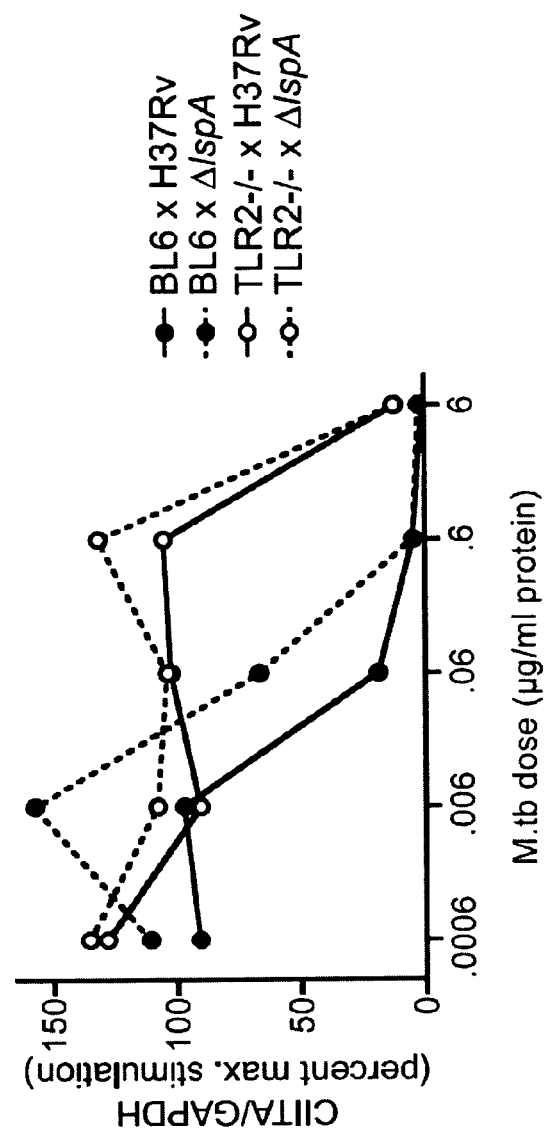

Macrophages Lacking TLR2 are More Resistant to *Mycobacterium Tuberculosis* Inhibition than Wild-Type Macrophages Having found that expression of mature lipoproteins was not required for *Mycobacterium tuberculosis* inhibition of macrophage responses to IFNγ, the contribution of TLR2 to the inhibitory effects of wild-type *Mycobacterium tuberculosis* and the ΔlspA mutant was tested. If all of TLR2 agonist activity of ΔlspA mutant was lost, as suggested by the 293-TLR2 cells, then one would expect to see no difference in *Mycobacterium tuberculosis* inhibition of TLR2$^{+/+}$ and TLR2$^{-/-}$ macrophages by the ΔlspA mutant and wild-type strains. Infection with either strain of *Mycobacterium tuberculosis* resulted in inhibition of IFNγ induction of CIITA mRNA in TLR2$^{-/-}$ macrophages, but a significantly higher MOI was required for TLR2$^{-/-}$ compared to TLR2$^{+/+}$ macrophages (FIG. 7A). To test a broader range of concentrations of *Mycobacterium tuberculosis*, the inhibition of IFNγ responsiveness of wild-type and TLR2$^{-/-}$ macrophages treated with *Mycobacterium tuberculosis* whole cell lysates (high inocula of live *Mycobacterium tuberculosis* result in death of macrophages) was also assayed. A significant difference in dose-response to *Mycobacterium tuberculosis* between the two types of macrophages was found (FIG. 7B). In contrast, there was relatively little difference in the inhibition caused by the wild-type and ΔlspA mutant strains of *Mycobacterium tuberculosis*. These results demonstrate that while *Mycobacterium tuberculosis* lipoprotein-TLR2 interactions contribute to inhibition of macrophage responses to IFNγ, they are not essential, and indicate that additional TLR2-dependent and TLR2-independent mechanisms of inhibition exist.

PIM, a Nonlipoprotein TLR2 Agonist, Inhibits Macrophage Response to IFNγ

Figure 8C:
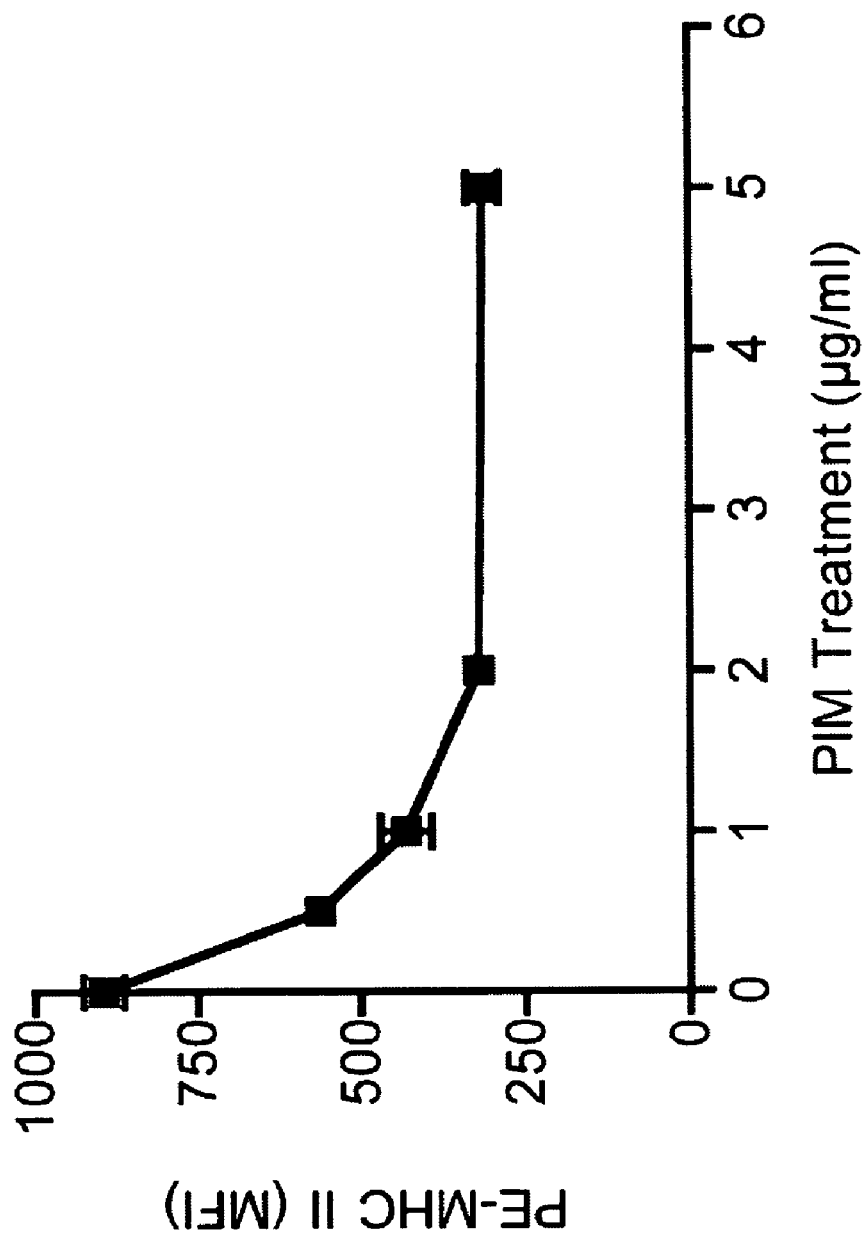

To examine the difference in sensitivity to TLR2 agonists between murine macrophages and 293-TLR2 cells, we compared the response of RAW264.7 and 293-TLR2 cells to lipopeptides and phosphatidyl inositol mannan$_{1+2}$ (PIM), a non-lipoprotein TLR2 agonist from *Mycobacterium tuberculosis*. 293-TLR2 cells responded to stimulation by 2 nM Pam$_3$CSK$_4$, a triacylated lipopeptide which signals via TLR2/TLR1 heterodimers, with secretion of IL-8, while 10, 1, or 0.1 µg/ml PIM (10 µg/ml PIM is ~5.6 µM) induced <1% as much IL-8 as Pam$_3$CSK$_4$ (FIG. 8A). 293-TLR2 cells also secreted significant amounts of IL-8 in response to nanomolar concentrations of Pam$_2$CSK$_4$, the diacylated analog on Pam₃CSK₄, and macrophage-activating lipopeptide-2, a diacylated lipopeptide which signals via TLR2/TLR6 heterodimers. RAW264.7 cells, by contrast, secreted similar amount of TNFα in response to 2 nM Pam₂CSK₄, 2 nM Pam₃CSK₄ and 5 μg/ml PIM (FIG. 8B). In addition, treatment of RAW264.7 cells with as little as 0.5 μg/ml PIM inhibited subsequent IFNγ induction of MHC class II surface expression (FIG. 8C). These results indicate that at least one nonlipoprotein TLR2 agonist which is not detected by 293-TLR2 cells is able to inhibit macrophage responses to IFNγ, and suggest that PIM and related mycobacterial cell wall glycolipids may be responsible for the effects of the ΔlspA strain on murine macrophages.

Inhibition of Macrophage Response to IFNγ Requires New Protein Synthesis

Figure 9A:
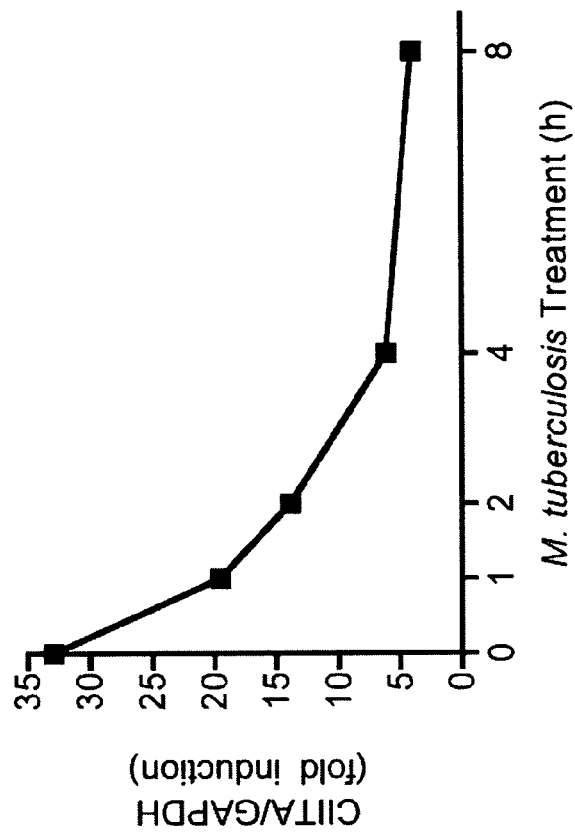
FIGS. 9A and 9B indicate that inhibition of macrophage response to IFNγ requires new protein synthesis.
Figure 9B:
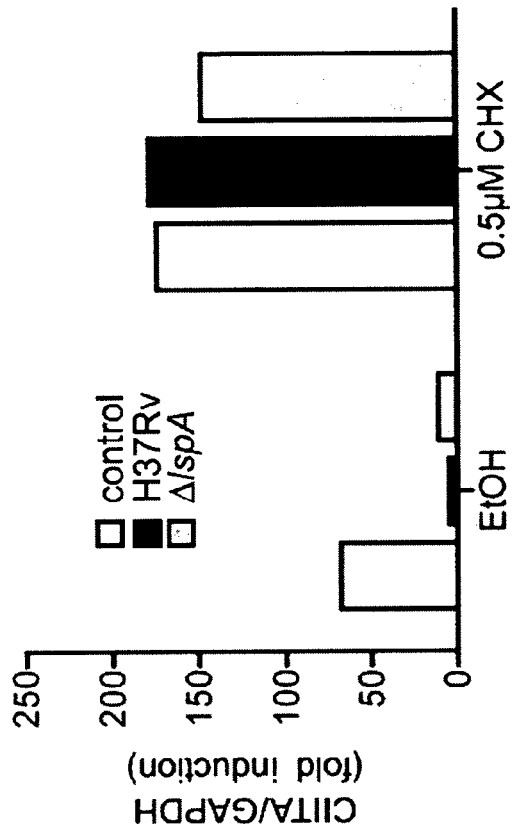

Much of the work on TLR2 and other innate pattern recognition receptors has focused on their proinflammatory activities, and has examined acute effects of innate immune activation. Since experiments reveal an inhibitory effect of innate immune activation on responses to IFNγ, the mechanism by which the observed inhibition occurs was investigated. It was found that 8 hours of pretreatment with *Mycobacterium tuberculosis* was required for maximal inhibition of responses to IFNγ (FIG. 9A). The need for extended pretreatment suggested that inhibition of the response to IFNγ requires new protein synthesis. Accordingly, cycloheximide (CHX) inhibition of macrophage protein synthesis prevented the ability of either wild-type *Mycobacterium tuberculosis* or the ΔlspA mutant strain to inhibit IFNγ induction of CIITA gene expression (FIG. 9B). These results indicate that although *Mycobacterium tuberculosis* stimulation of macrophages via innate immune receptors has an immediate proinflammatory effect, longer treatment with *Mycobacterium tuberculosis* induces the expression of one or more cellular proteins which inhibit macrophage responses to IFNγ.

C. Discussion

In efforts to understand the mechanisms whereby *Mycobacterium tuberculosis* evades elimination by an adaptive immune response, it has been discovered that *Mycobacterium tuberculosis* blocks macrophage responses to IFNγ, with consequences that include defective killing of *Mycobacterium tuberculosis* and class II antigen presentation.

Efforts to elucidate the mechanisms used by *Mycobacterium tuberculosis* to block macrophage responses to IFNγ have revealed that a purified 19 kDa bacterial lipoprotein, acting through TLR2 and MyD88, can initiate signals that disrupt IFNγ gene regulation. Moreover, it was found that peptidoglycan from *Mycobacterium tuberculosis* (or a component that copurifies with peptidoglycan) can act in a TLR2- and MyD88-independent manner to block responses to IFNγ. While substantial attention has been focused on the ability of the 19 kDa lipoprotein to inhibit responses to IFNγ and class II antigen presentation, a 19 kDa lipoprotein-null strain of BCG was as capable as a 19 kDa lipoprotein-replete strain at inhibiting class II antigen presentation by IFNγ-stimulated macrophages. Moreover, other lipoproteins and nonlipoprotein components of *Mycobacterium tuberculosis* can exhibit the same effects when examined as isolated components. This Example has used genetic modification of *Mycobacterium tuberculosis* to determine the relative roles of lipoproteins and nonlipoprotein components in inhibition of macrophage responses to IFNγ, in the context of the whole bacteria.

It reasoned that since acylation of a small synthetic lipopeptide was essential for inhibition of macrophage responses to IFNγ, disruption of prolipoprotein processing would provide valuable information on the relative role of *Mycobacterium tuberculosis* lipoproteins for inhibition of responses to IFNγ. Therefore, bacterial lipoprotein processing was disrupted by deleting the gene (lspA) that encodes the lipoprotein signal peptidase of *Mycobacterium tuberculosis*. It was found that the ΔlspA mutant strain lacked ≧95% of the TLR2 agonist activity of its parental strain, as assayed by a reporter cell line. Since whole-cell lysates of the ΔlspA mutant were also unable to stimulate 293-TLR2 cells, it does not appear that the lack of lipoprotein processing results only in sequestration of lipoproteins or other TLR2 agonists. It was also found that the ΔlspA mutant strain induced less TNFα secretion from murine macrophages than the wild type or complemented strains. This decreased induction of TNFα was most apparent after 8 and 12 h of *Mycobacterium tuberculosis* treatment. Extrapolation of the curves from the time course of treatment suggests that greater than 48 h of treatment would be required for the ΔlspA mutant to reach the level of TNFα induction of the wild type and complemented strains.

The relative importance and/or potency of lipoproteins in the inhibition of macrophage responses to IFNγ were then examined in the context of whole, live *Mycobacterium tuberculosis*. The ΔlspA strain exhibited no distinguishable difference in the potency or extent of inhibiting IFNγ induction of CIITA mRNA or surface MHC class II protein in macrophages, which indicates that lipoproteins are redundant in the context of inhibition by whole *Mycobacterium tuberculosis*.

In order to examine the contribution of TLR2-independent pathways in the inhibition of macrophage responses by whole *Mycobacterium tuberculosis*, the *Mycobacterium tuberculosis* inhibition of response to IFNγ in macrophages from $TLR2^{+/+}$ and $TLR2^{-/-}$ mice was compared. It was found that macrophages lacking TLR2 were significantly less sensitive to inhibition by *Mycobacterium tuberculosis* than wild-type macrophages. This difference in sensitivity was seen using both wild-type *Mycobacterium tuberculosis* and the ΔlspA mutant strain. This finding was surprising because it suggests that the 293-TLR2 cells do not respond well to non-lipoprotein TLR2 agonists in the ΔlspA mutant.

The responses of macrophages and 293-TLR2 cells to PIM were compared. PIM is a glycolipid purified from the cell wall of *Mycobacterium tuberculosis*, and has been shown to activate CHO cells expressing human TLR2. PIM activation of murine macrophages requires TLR2. It was found, however, that PIM did not activate 293-TLR2 cells, even when the cells were transfected with human CD36. Concentrations of PIM that potently induced TNFα secretion from macrophages did not induce significant IL-8 secretion from 293-TLR2 cells. In addition, concentrations of PIM unable to stimulate 293-TLR2 cells potently inhibited macrophage responses to IFNγ. These results suggest that, in the absence of mature lipoproteins, non-lipoprotein TLR2 agonists from *Mycobacterium tuberculosis* are able to inhibit macrophage responses to IFNγ. In addition to PIM, lipomannan from *Mycobacterium tuberculosis* has been reported to act as a nonlipoprotein TLR2 agonist. Peptidoglycans from gram-positive bacteria and BCG have also been shown to exhibit TLR2 agonist activity, although the interpretation of these results is controversial. It is likely that, although the 293-TLR2 cells respond to both diacylated and triacylated lipopeptides, they lack one or more coreceptors required to sense nonlipoprotein TLR2 agonists.

The preponderance of attention to TLR2 and other pattern-recognition receptors has been concentrated on activating signals that result in cytokine secretion and cellular phenotypic changes such as dendritic cell maturation. The finding that a later effect of TLR2 stimulation includes inhibition of IFNγ signaling, through induction of one or more proteins, extends the spectrum of activities attributable to innate immune receptors. While the results of this Example indicate that inhibition of IFNγ signaling is relieved by inhibition of protein synthesis, the essential protein(s) that mediates inhibition of responses to IFNγ has not yet been identified. One obvious candidate was suppressor of cytokine signaling-1 (SOCS1), which can be induced by *Mycobacterium tuberculosis* and which inhibits cellular responses to IFNγ by blocking the interaction of JAK1 and JAK2 with STAT1. However, the findings that *Mycobacterium tuberculosis* inhibits responses to IFNγ without inhibiting activation or function of STAT1 and that 19 kDa lipoprotein inhibits IFNγ-dependent MHC class II antigen presentation in macrophages from SOCS1-deficient mice provide evidence against a role for SOCS1 in this context. In addition, It appears that *Mycobacterium tuberculosis*-induced IL-6 can provide 'bystander' inhibition of IFNγ induction of MHC class II. To determine whether induction of IL-6 was sufficient for *Mycobacterium tuberculosis* inhibition of macrophage responses to IFNγ, the effects of *Mycobacterium tuberculosis* treatment on IL-6$^{-/-}$ BMDM was tested. Consistent with other observations, both C57BL/6 and IL6$^{-/-}$ BMDM treated with *Mycobacterium tuberculosis* had a defective response to IFNγ. These results indicate that although *Mycobacterium tuberculosis* stimulation of macrophages via innate immune receptors has an immediate proinflammatory effect, a late effect of innate immune receptor stimulation includes induction of one or more proteins which act to inhibit macrophage transcriptional responses to IFNγ. *Mycobacterium tuberculosis*, by virtue of its ability to survive in nonactivated macrophages, appears to have evolved mechanisms to take advantage of this late effect to enhance its survival in macrophages exposed to an important mediator of adaptive cellular immunity.

The foregoing description of the present invention provides illustration and description, but is not intended to be exhaustive or to limit the invention to the precise one disclosed. Modifications and variations consistent with the above teachings may be acquired from practice of the invention. Thus, it is noted that the scope of the invention is defined by the claims and their equivalents.

What is claimed is:

1. A modified *Mycobacterium tuberculosis* strain which lacks a functional lspA gene.

2. The modified *Mycobacterium tuberculosis* strain of claim 1 in which the lspA gene is deleted.

3. The modified *Mycobacterium tuberculosis* strain of claim 1, wherein said strain is a modified H37Ra or H37Rv strain.

4. The modified *Mycobacterium tuberculosis* strain of claim 1, wherein said strain comprises deletion or inactivation of one or more non-lspA genes.

5. The modified *Mycobacterium tuberculosis* strain of claim 4, wherein said strain has attenuated virulence as compared to a wild-type *Mycobacterium tuberculosis* strain.

6. A method for identifying *Mycobacterium tuberculosis* genes whose deletion or inactivation reduces *Mycobacterium tuberculosis* proinflammatory stimulation of macrophages, said method comprising:
    deleting or inactivating one non-lspA genes in a modified *Mycobacterium tuberculosis* strain of claim 1; and
    detecting TNFα secretion level by macrophages infected with said strain after said deleting or inactivating, wherein a reduction in said TNFα secretion level, as compared to a control TNFα secretion level, is indicative that deletion or inactivation of said one non-lspA gene reduces *Mycobacterium tuberculosis* proinflammatory stimulation of macrophages.

7. A method for identifying *Mycobacterium tuberculosis* genes whose deletion or inactivation reduces *Mycobacterium tuberculosis* inhibition of macrophage response to IFNγ, said method comprising:
    deleting or inactivating one non-lspA genes in a modified *Mycobacterium tuberculosis* strain of claim 1;
    infecting macrophages with said strain after said deleting or inactivating;
    contacting said infected macrophage with IFNγ; and
    detecting IFNγ response level of said macrophages after said contacting, wherein a reduction in said IFNγ response level, as compared to a control IFNγ response level, is indicative that deletion or inactivation of said one non-lspA genes reduces *Mycobacterium tuberculosis* inhibition of macrophage response to IFNγ.

8. The method of claim 7, wherein said IFNγ response level is determined by measuring MHC class II surface expression level or Class II transactivator mRNA level in said macrophages.

9. A method for identifying *Mycobacterium tuberculosis* genes whose deletion or inactivation reduces *Mycobacterium tuberculosis* Toll-like receptor 2 agonist activity, said method comprising:
    deleting or inactivating one non-lspA genes in a modified *Mycobacterium tuberculosis* strain of claim 1; and
    detecting Toll-like receptor 2 activation level in macrophages infected with said strain after said deleting or inactivating, wherein a reduction in said Toll-like receptor 2 activation level, as compared to a control Toll-like receptor 2 activation level, is indicative that deletion or inactivation of said one non-lspA genes reduces *Mycobacterium tuberculosis* Toll-like receptor 2 agonist activity.

10. A method for identifying *Mycobacterium tuberculosis* constituents capable of inhibiting macrophage response to IFNγ, said method comprising:
    isolating a constituent of a modified *Mycobacterium tuberculosis* strain of claim 1;
    contacting said constituent with macrophages; and
    detecting IFNγ response level of said macrophages after said contacting, wherein a reduction in said IFNγ response level, as compared to a control IFNγ response level, is indicative that said constituent is capable of inhibiting macrophage response to IFNγ.

11. The method of claim 10, wherein said constituent is a glycolipid.

12. A method for identifying Toll-like receptor 2 agonists, said method comprising:
    isolating a constituent of a modified *Mycobacterium tuberculosis* strain of claim 1;
    contacting one constituent with macrophages; and detecting Toll-like receptor 2 activation level in said macrophages after said contacting, wherein an increase in said Toll-like receptor 2 activation level, as compared to a control Toll-like receptor 2 activation level, is indicative that said constituent is a Toll-like receptor 2 agonist.

13. A method of treating or preventing *Mycobacterium tuberculosis* infection in a mammal, said method comprising administering to the mammal a modified *Mycobacterium tuberculosis* strain of claim 5 under conditions effective to treat *Mycobacterium tuberculosis* infection.

14. A method for identifying agents capable of reducing *Mycobacterium tuberculosis* inhibition of macrophage response to IFNγ, said method comprising:
  infecting macrophages with a modified *Mycobacterium tuberculosis* strain of claim 1;
  contacting the macrophages with an agent of interest; and
  detecting IFNγ response level of said macrophages after said contacting, wherein an increase in said IFNγ response level, as compared to a control IFNγ response level, is indicative that said agent is capable of reducing *Mycobacterium tuberculosis* inhibition of macrophage response to IFNγ.

15. A method of isolating components for adjuvant therapy, said method comprising:
  disrupting a modified *Mycobacterium tuberculosis* strain of claim 1;
  fractionating components of said strain; and
  isolating one or more cell wall components from the fractionated components for adjuvant therapy.

16. The method according to claim 15, wherein said isolating is carried out by extraction.

17. The method according to claim 16, wherein the extraction comprises chemical or enzymatic cleavage.

* * * * *

SEQUENCE LISTING

```
<160> NUMBER OF SEQ ID NOS: 13

<210> SEQ ID NO 1
<211> LENGTH: 26
<212> TYPE: DNA
<213> ORGANISM: Artificial
<220> FEATURE:
<223> OTHER INFORMATION: PCR forward primer

<400> SEQUENCE: 1
cttaagatcg ctcccgtctc gacagt                                26

<210> SEQ ID NO 2
<211> LENGTH: 26
<212> TYPE: DNA
<213> ORGANISM: Artificial
<220> FEATURE:
<223> OTHER INFORMATION: PCR reverse primer

<400> SEQUENCE: 2
tctagagcgg atcagccgat cctgtt                                26

<210> SEQ ID NO 3
<211> LENGTH: 26
<212> TYPE: DNA
<213> ORGANISM: Artificial
<220> FEATURE:
<223> OTHER INFORMATION: PCR forward primer

<400> SEQUENCE: 3
aagcttacac cgtaggtcgg cgcaaa                                26

<210> SEQ ID NO 4
<211> LENGTH: 26
<212> TYPE: DNA
<213> ORGANISM: Artificial
<220> FEATURE:
<223> OTHER INFORMATION: PCR reverse primer

<400> SEQUENCE: 4
actagtgccg tgctcaactg gaaagg                                26
```

<210> SEQ ID NO 5
<211> LENGTH: 26
<212> TYPE: DNA
<213> ORGANISM: Artificial
<220> FEATURE:
<223> OTHER INFORMATION: PCR forward primer

<400> SEQUENCE: 5
tctagagcaa gcgcgtcgcg cagatt                                    26

<210> SEQ ID NO 6
<211> LENGTH: 26
<212> TYPE: DNA
<213> ORGANISM: Artificial
<220> FEATURE:
<223> OTHER INFORMATION: PCR reverse primer

<400> SEQUENCE: 6
aagcttaacc gcacctgcag caaggc                                    26

<210> SEQ ID NO 7
<211> LENGTH: 20
<212> TYPE: DNA
<213> ORGANISM: Artificial
<220> FEATURE:
<223> OTHER INFORMATION: Reverse transcription PCR primer

<400> SEQUENCE: 7
cgacctacgg tgtcgaagtc                                           20

<210> SEQ ID NO 8
<211> LENGTH: 20
<212> TYPE: DNA
<213> ORGANISM: Artificial
<220> FEATURE:
<223> OTHER INFORMATION: PCR forward primer

<400> SEQUENCE: 8
cctggactct ggtgcgtaat                                           20

<210> SEQ ID NO 9
<211> LENGTH: 20
<212> TYPE: DNA
<213> ORGANISM: Artificial
<220> FEATURE:
<223> OTHER INFORMATION: PCR reverse primer

<400> SEQUENCE: 9
accgacaaga aatcgacgac                                           20

<210> SEQ ID NO 10
<211> LENGTH: 24
<212> TYPE: DNA
<213> ORGANISM: Artificial
<220> FEATURE:
<223> OTHER INFORMATION: PCR forward primer

<400> SEQUENCE: 10
gaagttcacc attgagccat ttaa                                      24

<210> SEQ ID NO 11
<211> LENGTH: 20
<212> TYPE: DNA
<213> ORGANISM: Artificial
<220> FEATURE:
<223> OTHER INFORMATION: PCR reverse primer -continued

```
<400> SEQUENCE: 11
ctgggtctgc acgagacgat                                              20

<210> SEQ ID NO 12
<211> LENGTH: 20
<212> TYPE: DNA
<213> ORGANISM: Artificial
<220> FEATURE:
<223> OTHER INFORMATION: PCR forward primer

<400> SEQUENCE: 12
tgtgtccgtc gtggatctga                                              20

<210> SEQ ID NO 13
<211> LENGTH: 21
<212> TYPE: DNA
<213> ORGANISM: Artificial
<220> FEATURE:
<223> OTHER INFORMATION: PCR reverse primer

<400> SEQUENCE: 13
cctgcttcac caccttcttg a                                            21
```